(12) United States Patent
Foley et al.

(10) Patent No.: US 9,096,630 B2
(45) Date of Patent: Aug. 4, 2015

(54) AMPHIPHILIC COMPOSITIONS AND METHODS FOR PREPARING AND USING SAME

(75) Inventors: Patrick Foley, New Haven, CT (US); Paul Anastas, Guilford, CT (US); Toby Sommer, New Haven, CT (US)

(73) Assignee: Yale University, New Haven, CT (US)

( * ) Notice: Subject to any disclaimer, the term of this patent is extended or adjusted under 35 U.S.C. 154(b) by 386 days.

(21) Appl. No.: 13/505,953

(22) PCT Filed: Nov. 8, 2010

(86) PCT No.: PCT/US2010/055831
§ 371 (c)(1),
(2), (4) Date: May 3, 2012

(87) PCT Pub. No.: WO2011/057192
PCT Pub. Date: May 12, 2011

(65) Prior Publication Data
US 2012/0225832 A1    Sep. 6, 2012

Related U.S. Application Data

(60) Provisional application No. 61/258,860, filed on Nov. 6, 2009, provisional application No. 61/356,173, filed on Jun. 18, 2010.

(51) Int. Cl.
| | | |
|---|---|---|
| *C07H 7/04* | (2006.01) | |
| *C07H 1/00* | (2006.01) | |
| *C07H 7/02* | (2006.01) | |
| *C07D 309/04* | (2006.01) | |
| *C07D 309/10* | (2006.01) | |
| *C11D 3/22* | (2006.01) | |

(52) U.S. Cl.
CPC .............. *C07H 7/02* (2013.01); *C07D 309/04* (2013.01); *C07D 309/10* (2013.01); *C07H 7/04* (2013.01); *C11D 3/221* (2013.01)

(58) Field of Classification Search
CPC .................................................... C07D 309/10
See application file for complete search history.

(56) References Cited

U.S. PATENT DOCUMENTS

| | | |
|---|---|---|
| 5,419,898 A | 5/1995 | Ikejiri et al. |
| 7,732,414 B2 | 6/2010 | Dalko et al. |
| 7,862,804 B2 | 1/2011 | Rolland |
| 2007/0081956 A1 | 4/2007 | Rolland |

FOREIGN PATENT DOCUMENTS

WO    WO-02051803 A2    7/2002

OTHER PUBLICATIONS

Wang, J.-f. et al., Tetrahedron, "A novel and efficient direct aldol condensation from ketones and aromatic aldehydes catalyzed by proline-TEA through a new pathway", 2009, vol. 65, pp. 4826-4833.*
Dembitsky. "Astonishing Diversity of Natural Surfactants: 7. Biologically Active Hemi-and Monoterpenoid Glycosides." *Lipids.* 41.1(2006):1-27.
Demibtsky. "Astonishing Diversity of Natural Surfactants: 1. Glycosides of Fatty Acids and Alcohols." *Lipids.* 39.10(2003):933-953.
Du et al. "Recent Advances in Stereoselective C-Glycoside Synthesis." *Tetrahedron.* 54(1998):9913-9959.
Foley et al. "Linear and Cyclic C-Glycoside as Surfactants." *Green Chem.* 13(2011):321-325.
Hejchman et al. "Synthesis and Cytotoxicity of Water-Soluble Ambrosin Prodrug Candidates." *J. Med. Chem.* 38(1995):3407-3410.
Lay et al. "Synthesis of Antimetabolites of Sucrose." *J. Chem. Soc. Perkin Trans. 1* (1994):333-338.
Lüders. "Chemical Properties and Derivation of Surface-Active Alkyl Glucosides and Alkyl Polyglycosides." *Nonionic Sufactants.* Boca Raton, Florida: CRC Press. Balzer et al., eds. (2000):77-83.
Wang et al. "Epimerization of 2'-Carbonylalkyl-C-Glycosides via Enolation, β-Elimination and Intramolecular Cycloaddition." *J. Org. Chem.* 68.21(2003):8097-8105.

* cited by examiner

*Primary Examiner* — Layla Bland
*Assistant Examiner* — Bahar Craigo
(74) *Attorney, Agent, or Firm* — Mintz Levin Cohn Ferris Glovsky and Popeo, P.C.; Muriel Liberto; Shovon Ashraf

(57) ABSTRACT

The invention relates to amphiphilic C-glycoside derivatives, to methods of using them and to processes for synthesizing them. Specifically, the invention relates to novel cyclic and linear enone-glycolipids and cyclic ketone-glycolipids.

36 Claims, 1 Drawing Sheet

AMPHIPHILIC COMPOSITIONS AND METHODS FOR PREPARING AND USING SAME

RELATED APPLICATIONS

This application is a national stage application, filed under 35 U.S.C. §371 of International Application No. PCT/US2010/055831, filed Nov. 8, 2010, which claims priority to U.S. Provisional Patent Application Ser. Nos. 61/258,860 and 61/356,173, filed Nov. 6, 2009 and Jun. 18, 2010, respectively. The entire contents of each application are incorporated by reference herein.

BACKGROUND OF THE INVENTION

Surfactants reduce the surface tension of water by adsorbing at the liquid-gas interface. They also reduce the interfacial tension between oil and water by adsorbing at the liquid-liquid interface. Many surfactants can also assemble in the bulk solution into aggregates. Examples of such aggregates are vesicles and micelles. The concentration at which surfactants begin to form micelles is known as the critical micelle concentration or CMC. When micelles form in water, their tails form a core that can encapsulate an oil droplet, and their (ionic/polar) heads form an outer shell that maintains favorable contact with water. When surfactants assemble in oil, the aggregate is referred to as a reverse micelle. In a reverse micelle, the heads are in the core and the tails maintain favorable contact with oil. Surfactants are also often classified into four primary groups; anionic, cationic, non-ionic, and zwitterionic (dual charge).

Thermodynamics of the surfactant systems are of great importance, theoretically and practically. This is because surfactant systems represent systems between ordered and disordered states of matter. Surfactant solutions may contain an ordered phase (micelles) and a disordered phase (free surfactant molecules and/or ions in the solution).

Surfactants play an important role in many practical applications and products, including: detergents; fabric softener; emulsifiers and emulsions; paints; adhesives; inks; anti-fogging compositions; soil remediation; dispersants; wetting agents; ski wax, snowboard wax; deinking of recycled paper, both in flotation, washing and enzymatic processes; foaming agents; defoamers; laxatives; agrochemical formulations; herbicides; some insecticides; quantum dot coating; biocides (sanitizers); shampoo; hair conditioners; spermicide; firefighting; liquid drag reducing agents in pipelines; alkali surfactant polymers used to mobilize oil in oil wells; ferrofluids; leak detectors, etc.

Some surfactants are known to be toxic to animals, ecosystems and humans, and can increase the diffusion of other environmental contaminants.

Accordingly, new safe, non-toxic surfactants and methods for their use are needed. The present invention addresses these needs.

SUMMARY OF THE INVENTION

The invention relates to amphiphilic molecules and uses thereof. For Example, the invention relates to novel linear C-glycoside enone derivatives of formula A, to methods of using them and to processes for synthesizing them:

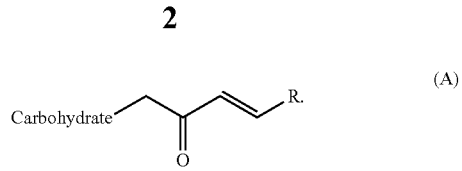

In one aspect, the invention relates to novel linear enone-glycolipids.

The invention relates to a novel class of compounds having a polar head group and a non-polar tail linked by an enone moiety. For example, a compound of the invention can include a carbohydrate moiety linked to a lipid via an enone, according to formula (I):

(I)

Sugar ⟶ ⟶ Lipid.
       O

Compounds according to formula I are amphiphilic, having both hydrophobic and hydrophilic components. Such molecules have a broad range of applications as surface active agents (i.e., surfactants) and/or polymer precursors.

These enones are thought to possess unique physical properties, such as rigidity and reactivity that can be exploited for various applications. The molecules are C-glycosides bearing a C-glycosidic linkage instead of an O-glycosidic linkage between the carbohydrate and R (lipid) moieties, thus enhancing the stability of the glycolipid.

The invention also relates, in part, to a novel synthesis of linear enone-glycoside (e.g., glycolipid) compounds.

Thus, the invention relates to a compound of formula A:

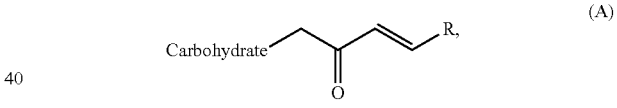

wherein Carbohydrate is a C-linked glycoside, and R is hydrogen, linear alkyl, branched alkyl, substituted linear alkyl, substituted branched alkyl, cycloalkyl, or substituted cycloalkyl. The term "glycoside" refers to both sugar and sugar derivatives unless otherwise specified. Examples include a monosaccharide, a polysaccharide (e.g., a disaccharide), and their glycosides such as alkyl-, acyl-, sulfate-, or phosphate-glycosides. As defined herein, the term "sugar derivative" refers to a compound that has a sugar moiety bonded to a non-carbohydrate moiety such as alkyl, amino, lipid, or peptide, or a sugar whose one or more hydroxyl groups are replaced by or subjected to modification or reaction to form other functional groups described herein. Typical derivatization reactions offered by hydroxyl groups are oxidation, esterification, and ether formation.

For example, in the compound of formula A, R is saturated or unsaturated alkyl. R can have, for example, one or more degrees of unsaturation. In some compounds, R contains one degree of unsaturation, e.g., one double bond.

In certain compounds of the invention R is an aliphatic chain of a fatty acid. In certain compounds, R is alkyl having 4, 5, 6, 7, 8, 9, 10, 11, 12, 13, 14, 15, 16, 17, 18, 19, 20, 21, 22, 23, or 24 carbon atoms, for example 6, 7, 8, 9, 10, 11, or 12 carbon atoms, or, for example, 13, 14, 15, 16, 17, 18, 19, 20, 21, or 22 carbon atoms. For example, R is undecane.

In certain compounds of the invention, Carbohydrate is a mono- or polysaccharide (e.g., disaccharide), either derivatized (i.e., a corresponding glycoside such as alkyl-, acyl-, sulfate-, or phosphate-glycoside) or underivatized. Carbohydrate can be, for example, glucose, xylose, lyxose, mannose, maltose, cellobiose, galactose, or a glycosidic derivative thereof. In certain compounds, Carbohydrate is glucose or glucoside.

In some compounds of the invention, Carbohydrate is derived from a biomass fraction.

Compounds of formula A include compounds of formula I:

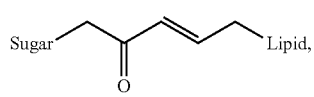

(I)

wherein Sugar is a C-linked glycoside and Lipid is selected from fats, waxes, sterols, fat-soluble vitamins, monoglycerides, diglycerides, phospholipids, and fatty acids.

In certain compounds of formula I, Lipid is an aliphatic chain of a fatty acid. For example, the fatty acid chain can have 4, 5, 6, 7, 8, 9, 10, 11, 12, 13, 14, 15, 16, 17, 18, 19, 20, 21, 22, 23, or 24 carbon atoms, for example 6, 7, 8, 9, 10, 11, or 12 carbon atoms, or, for example, 13, 14, 15, 16, 17, 18, 19, 20, 21, or 22 carbon atoms. In some compounds, the fatty acid chain has 11 carbon atoms.

In some compounds of the invention, Sugar is a mono- or polysaccharide (e.g., disaccharide), either derivatized (i.e., a corresponding glycoside) or underivatized. Sugar can be, for example, glucose, xylose, lyxose, mannose, maltose, cellobiose, galactose, or a glycosidic derivative thereof. In certain compounds, Sugar is glucose or glucoside. In other compounds, Sugar is derived from a biomass fraction.

In some compounds, Sugar is a monosaccharide (or its derivative) and Lipid is an aliphatic chain of a fatty acid.

In some compounds, Lipid is a fat-soluble vitamin, e.g., a vitamin selected from A, D, E, and K.

One subset of compounds of the invention includes those of formula Ia:

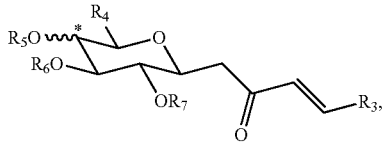

(Ia)

wherein $R_3$ is H, or $C_1$-$C_{24}$ alkyl optionally substituted with $COOR_a$, $R_a$ being H, $C_1$-$C_{10}$ saturated or unsaturated alkyl, $C_3$-$C_8$ cycloalkyl, aryl, or heteroaryl; $R_4$ is $CH_2OR_b$ or $COOR_b$, in which $R_b$ is H, sulfo, sulfonato, phosphono, phosphonato, $COR_c$, $R_c$ being hydroxy, $C_1$-$C_{10}$ alkoxy, or $C_1$-$C_{10}$ saturated or unsaturated alkyl optionally substituted with one or more groups selected from carboxy, carboxylato, sulfo, sulfonato, phosphono, and phosphonato, or $R_b$ is $C_1$-$C_{10}$ saturated or unsaturated alkyl optionally substituted with one or more groups selected from carboxy, carboxylato, sulfo, sulfonato, phosphono, phosphonato, —(CH$_2$CH$_2$O)$_n$H, and —(CH$_2$CHOHCH$_2$O)$_n$H, n being 1, 2, 3, 4, 5, 6, 7, 8, 9, or 10; and each of $R_5$, $R_6$, and $R_7$, independently, is H, sulfo, sulfonato, phosphono, phosphonato, $COR_c$, a monosaccharide or a glycosidic derivative thereof, or $C_1$-$C_{10}$ saturated or unsaturated alkyl optionally substituted with one or more groups selected from carboxy, carboxylato, sulfo, sulfonato, phosphono, phosphonato, —(CH$_2$CH$_2$O)$_n$H, and —(CH$_2$CHOHCH$_2$O)$_n$H.

In some compounds of formula Ia above, $R_3$ is $C_6$-$C_{22}$ alkyl optionally substituted with $COOR_a$. In these compounds, at least one of $R_5$, $R_6$, and $R_7$ is sulfo, sulfonato, phosphono, phosphonato, $COR_c$, a monosaccharide or a glycosidic derivative thereof, or $C_1$-$C_{10}$ alkyl optionally substituted with one or more groups selected from carboxy, carboxylato, sulfo, sulfonato, phosphono, phosphonato, —(CH$_2$CH$_2$O)$_n$H, and —(CH$_2$CHOHCH$_2$O)$_n$H and the others are each hydrogen; $R_4$ is $CH_2OR_b$ and at least one of $R_b$, $R_5$, $R_6$, and $R_7$ is sulfa, sulfonato, phosphono, phosphonato, $COR_c$, or $C_1$-$C_{10}$ alkyl optionally substituted with one or more groups selected from carboxy, carboxylato, sulfo, sulfonato, phosphono, phosphonato, —(CH$_2$CH$_2$O)$_n$H, and —(CH$_2$CHOHCH$_2$O)$_n$H and the others are each hydrogen; or $R_b$, $R_5$, $R_6$, and $R_7$ are each hydrogen.

Still in some compounds of formula Ia above, at least one of $R_5$, $R_6$, and $R_7$ is sulfo, sulfonato, phosphono, phosphonato, $COR_c$, a monosaccharide or a glycosidic derivative thereof, or $C_1$-$C_{10}$ alkyl optionally substituted with one or more groups selected from carboxy, carboxylato, sulfo, sulfonato, phosphono, phosphonato, —(CH$_2$CH$_2$O)$_n$H, and —(CH$_2$CHOHCH$_2$O)$_n$H and the others are each hydrogen; or $R_4$ is $CH_2OR_b$ and at least one of $R_b$, $R_5$, $R_6$, and $R_7$ is sulfo, sulfonato, phosphono, phosphonato, $COR_c$, or $C_1$-$C_{10}$ alkyl optionally substituted with one or more groups selected from carboxy, carboxylato, sulfo, sulfonato, phosphono, phosphonato, —(CH$_2$CH$_2$O)$_n$H, and —(CH$_2$CHOHCH$_2$O)$_n$H and the others are each hydrogen; or $R_b$, $R_5$, $R_6$, and $R_7$ are each hydrogen.

One compound of the invention, Compound 1, has the formula:

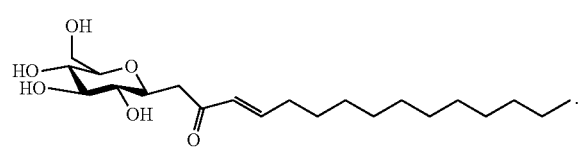

(1)

The invention also relates, in part to compositions comprising the compounds of the invention, e.g., a compound of formula A or formula I.

The invention relates, in part to a method of synthesizing a compound of formula A:

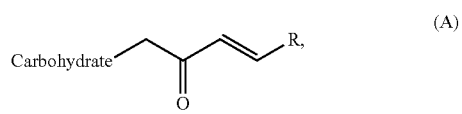

(A)

where Carbohydrate is a C-linked glycoside, and R is hydrogen, linear alkyl, branched alkyl, substituted linear alkyl, substituted branched alkyl, cycloalkyl, or substituted cycloalkyl. The method includes (a) reacting a carbohydrate with a 1,3-diketone in water in a mildly alkaline aqueous solution to form a C-glycoside intermediate,

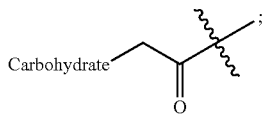

and (b) reacting the C-glycoside intermediate with an aldehyde in the presence of a catalyst to form an enone glycoside of formula A.

For example, in the compound of formula A synthesized by the method of the invention, R is saturated or unsaturated alkyl. R can have, for example, one or more degrees of unsaturation. In some compounds, R contains one degree of unsaturation, e.g., one double bond.

In certain methods of the invention R is an aliphatic chain of a fatty acid. In certain methods, R is alkyl having 4, 5, 6, 7, 8, 9, 10, 11, 12, 13, 14, 15, 16, 17, 18, 19, 20, 21, 22, 23, or 24 carbon atoms, for example 6, 7, 8, 9, 10, 11, or 12 carbon atoms, or, for example, 13, 14, 15, 16, 17, 18, 19, 20, 21, or 22 carbon atoms. For example, R is undecane. In one aspect, R is a lipid.

In certain methods of the invention, Carbohydrate is a mono- or polysaccharide or a glycosidic derivative thereof. Carbohydrate can be, for example, glucose, xylose, lyxose, mannose, maltose, cellobiose, or galactose. In certain methods, Carbohydrate is glucose or glucoside.

In some methods of the invention, Carbohydrate is derived from a biomass fraction.

The methods of the invention can be used to synthesize a compound of formula I:

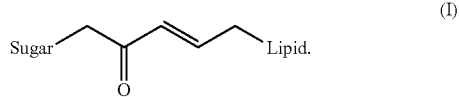

(I)

In the method of the invention, the catalyst can be, for example, pyrrolidine.

In the method of the invention, the diketone reactant can be acetylacetone.

The synthetic method of the invention can further include purification of the C-glycoside intermediate prior to step (b), and/or purification the enone glycoside of formula A.

The method of the invention can be used to synthesize the enone glycoside

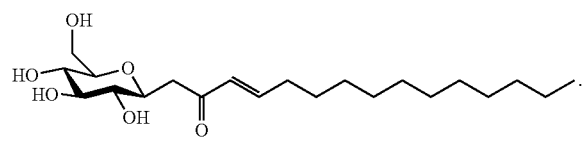

The invention also relates, in part to a method of synthesizing a reactive polymer precursor of the formula

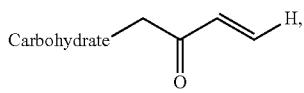

wherein Carbohydrate is a C-linked glycoside. The method includes (a) reacting a carbohydrate with a 1,3-diketone in water in a mildly alkaline aqueous solution to form a C-glycoside intermediate,

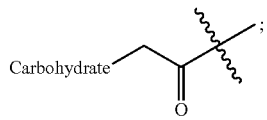

and (b) reacting the C-glycoside intermediate with formaldehyde in the presence of a catalyst to form an enone glycoside of the formula

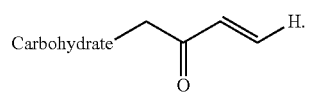

In this method, Carbohydrate can be a mono- or polysaccharide or a glycoside thereof. For example, the catalyst can be pyrrolidine. In some embodiments of this method, the diketone reactant is acetylacetone.

The invention also relates to novel cyclic amphiphilic compounds of formula B, to methods of using them and to processes for synthesizing them:

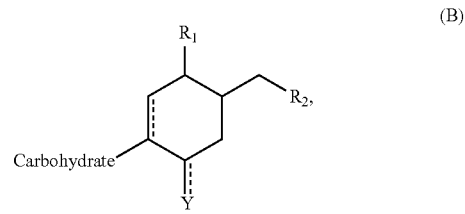

wherein Carbohydrate is a C-linked glycoside; each of $R_1$, and $R_2$, independently, is hydrogen, linear alkyl, branched alkyl, substituted linear alkyl, substituted branched alkyl, cycloalkyl, or substituted cycloalkyl, each of the two dotted lines ------, independently, is absent or a bond, and Y is O or $OR_8$, in which $R_8$ is hydrogen or $C_1$-$C_{10}$ alkyl. In particular, the cyclic amphiphilic compounds are of the following formula:

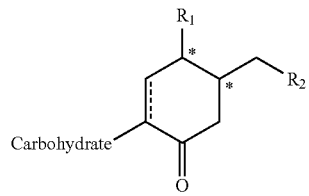

The invention relates to the compound, wherein $R_1$ and $R_2$ are each independently selected from saturated or unsaturated alkyl. In part, the invention relates to a compound wherein $R_1$ and $R_2$ are each an aliphatic chain of a fatty acid. In part, the invention relates to a compound wherein $R_1$ and $R_2$ are each an alkyl group having 2, 3, 4, 5, 6, 7, 8, 9, or 10 carbon atoms. In part, the invention relates to a compound wherein $R_1$ and $R_2$ are each an alkyl group having 2, 3, 4, 5, or 6 carbon atoms.

The invention relates to the compound of formula B, wherein Carbohydrate is a mono- or polysaccharide (e.g., disaccharide), either derivatized (i.e., a corresponding glycoside such as alkyl-, acyl-, sulfate-, or phosphate-glycoside) or underivatized. In part, the invention relates to a compound wherein the Carbohydrate is selected from glucose, xylose, lyxose, mannose, maltose, cellobiose, galactose, and a glycosidic derivative thereof. In part, the invention relates to a compound wherein the Carbohydrate is glucose or glucoside. In part, the invention relates to a compound wherein Carbohydrate that is derived from a biomass fraction. In part, the invention relates to a compound wherein the two dotted lines are both absent in a compound of formula B. In part, the invention relates to a compound wherein both the dotted lines are each a bond in a compound of formula B. In part, the invention relates to a compound wherein the one of the two dotted lines is absent and the other is a bond in a compound of formula B, e.g., Y being O and the dotted line connecting to Y being a bond.

One subset of the compounds of formula B are those of formula Ib:

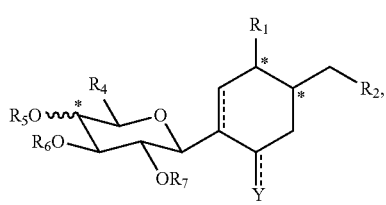

wherein each of $R_1$ and $R_2$ independently is H, or $C_1$-$C_{24}$ alkyl optionally substituted with $COOR_a$, $R_a$ being H, $C_1$-$C_{10}$ alkyl, $C_3$-$C_8$ cycloalkyl, aryl, or heteroaryl; $R_4$ is $CH_2OR_b$ or $COOR_b$, in which $R_b$ is H, sulfo, sulfonato, phosphono, phosphonato, $COR_c$, $R_c$ being hydroxy, $C_1$-$C_{10}$ alkoxy, or $C_1$-$C_{10}$ alkyl optionally substituted with one or more groups selected from carboxy, carboxylato, sulfo, sulfonato, phosphono, and phosphonato, or $R_b$ is $C_1$-$C_{10}$ alkyl optionally substituted with one or more groups selected from carboxy, carboxylato, sulfa, sulfonato, phosphono, phosphonato, —(CH$_2$CH$_2$O)$_n$H, and —(CH$_2$CHOHCH$_2$O)$_n$H, n being 1, 2, 3, 4, 5, 6, 7, 8, 9, or 10; and each of $R_5$, $R_6$, and $R_7$, independently, is H, sulfo, sulfonato, phosphono, phosphonato, $COR_c$, a monosaccharide or a glycosidic derivative thereof, or $C_1$-$C_{10}$ alkyl optionally substituted with one or more groups selected from carboxy, carboxylato, sulfo, sulfonato, phosphono, phosphonato, —(CH$_2$CH$_2$O)$_n$H, and —(CH$_2$CHOHCH$_2$O)$_n$H.

In part, this invention relates to compounds of formula Ib above, in which each of $R_1$ and $R_2$, independently is $C_1$-$C_{22}$ alkyl (e.g., $C_2$-$C_5$ alkyl, $C_6$-$C_{13}$ alkyl, or $C_{14}$-$C_{22}$ alkyl) optionally substituted with $COOR_a$. In these compounds, at least one of $R_5$, $R_6$, and $R_7$ is sulfo, sulfonato, phosphono, phosphonato, $COR_c$, a monosaccharide or a glycosidic derivative thereof, or $C_1$-$C_{10}$ alkyl optionally substituted with one or more groups selected from carboxy, carboxylato, sulfo, sulfonato, phosphono, phosphonato, —(CH$_2$CH$_2$O)$_n$H, and —(CH$_2$CHOHCH$_2$O)$_n$H and the others are each hydrogen; $R_4$ is $CH_2OR_b$ and at least one of $R_b$, $R_5$, $R_6$, and $R_7$ is sulfo, sulfonato, phosphono, phosphonato, $COR_c$, or $C_1$-$C_{10}$ alkyl optionally substituted with one or more groups selected from carboxy, carboxylato, sulfo, sulfonato, phosphono, phosphonato, —(CH$_2$CH$_2$O)$_n$H, and —(CH$_2$CHOHCH$_2$O)$_n$H and the others are each hydrogen; or $R_b$, $R_5$, $R_6$, and $R_7$ are each hydrogen.

Still in some compounds of formula Ib above, at least one of $R_5$, $R_6$, and $R_7$ is sulfo, sulfonato, phosphono, phosphonato, $COR_c$, a monosaccharide or a glycosidic derivative thereof, or $C_1$-$C_{10}$ alkyl optionally substituted with one or more groups selected from carboxy, carboxylato, sulfo, sulfonato, phosphono, phosphonato, —(CH$_2$CH$_2$O)$_n$H, and —(CH$_2$CHOHCH$_2$O)$_n$H and the others are each hydrogen; or $R_4$ is $CH_2OR_b$ and at least one of $R_b$, $R_5$, $R_6$, and $R_7$ is sulfo, sulfonato, phosphono, phosphonato, $COR_c$, or $C_1$-$C_{10}$ alkyl optionally substituted with one or more groups selected from carboxy, carboxylato, sulfo, sulfonato, phosphono, phosphonato, —(CH$_2$CH$_2$O)$_n$H, and —(CH$_2$CHOHCH$_2$O)$_n$H and the others are each hydrogen; or $R_b$, $R_5$, $R_6$, and $R_7$ are each hydrogen.

In part, the invention relates to a compound of formula Ib, in which R5 is a monosaccharide or a glycosidic derivative thereof.

In part, the invention relates to a compound of formula Ib, in which R5 is glucose, xylose, lyxose, mannose, galactose, or a glycosidic derivative thereof.

In part, the invention relates to a compound of formula Ib, in which Y is O.

In part, the invention relates to a compound of formula Ib, in which Y is OH.

Another subset of the compounds of formula B are cyclic compounds of formula II

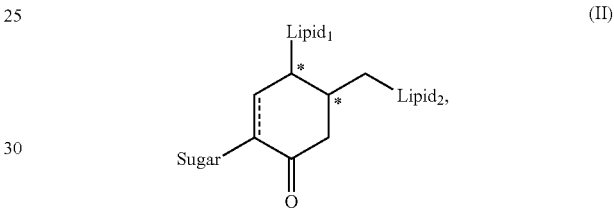

wherein Sugar is a C-linked glycoside; the dotted line ------ is absent or a bond, and Lipid$_1$ and Lipid$_2$ are each, independently selected from fats, waxes, sterols, fat-soluble vitamins, monoglycerides, diglycerides, phospholipids, and fatty acids.

The invention relates to a compound, wherein Lipid$_1$ and Lipid$_2$ are each independently an aliphatic chain of a fatty acid, same or different. In part, the invention relates to a compound wherein the aliphatic chain of a fatty acid has 2, 3, 4, 5, 6, 7, 8, 9, or 10 carbon atoms. In part, the invention relates to a compound, wherein the aliphatic chain of a fatty acid has 2, 3, 4, 5, or 6 carbon atoms.

The invention relates to a compound wherein Sugar is a mono- or polysaccharide (e.g., disaccharide), either derivatized (i.e., a corresponding glycoside) or underivatized. Sugar can be, for example, glucose, xylose, lyxose, mannose, maltose, cellobiose, galactose, or a glycosidic derivative thereof. In certain compounds, Sugar is glucose or glucoside. In certain compounds of the invention, the Sugar is derived from a biomass fraction. In certain compounds, the Sugar is a monosaccharide (or its derivatives) and Lipid$_1$ and Lipid$_2$ are each an aliphatic chain of a fatty acid.

The invention relates to a compound selected from:

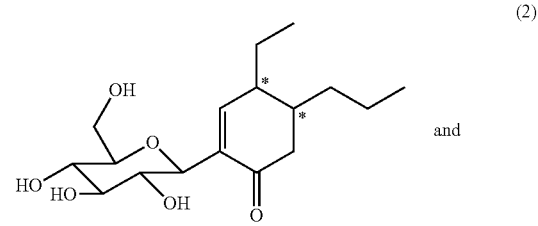

and

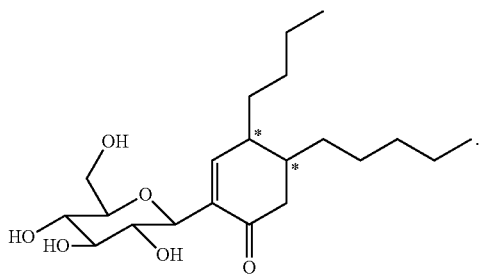

(3)

The invention also relates, in part to compositions comprising a cyclic compound of the invention e.g., a compound of formula B or II.

The invention relates, in part to a method of synthesizing a cyclic compound of formula B:

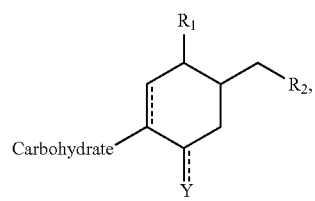

(B)

wherein Carbohydrate is a C-linked glycoside, each of $R_1$, and $R_2$, independently, is hydrogen, linear alkyl, branched alkyl, substituted linear alkyl, substituted branched alkyl, cycloalkyl, or substituted cycloalkyl, each of the two dotted lines ------, independently, is absent or a bond, and Y is O or $OR_8$, in which $R_8$ is hydrogen or $C_1$-$C_{10}$ alkyl. The method comprising: reacting a carbohydrate-containing ketone with excess aldehyde in an alkaline solution to form a compound of formula B in which each of the dotted lines is a bond and Y is O.

In certain methods of the invention, the Carbohydrate is a mono- or polysaccharide, either derivatized or underivatized. In certain methods of the invention, the Carbohydrate is selected from glucose, xylose, lyxose, mannose, maltose, cellobiose, galactose and a glycosidic derivative thereof. In certain methods of the invention, the Carbohydrate is glucose or glucoside. In certain methods of the invention, the Carbohydrate is derived from a biomass fraction.

In certain methods of the invention, $R_1$ and $R_2$ are each lipids. In certain methods, $R_1$ is a lipid. In certain methods, $R_2$ is a lipid. In certain methods of the invention $R_1$ and $R_2$ are each an aliphatic chain of a fatty acid. In certain methods, $R_1$ and $R_2$ are each alkyl having 2, 3, 4, 5, 6, 7, 8, 9, or 10 carbon atoms. In certain methods, $R_1$ and $R_2$ are each alkyl having 2, 3, 4, 5, or 6 carbon atoms. The methods of the invention may further include reducing the compound of formula B in which each of the dotted lines is a bond and Y is O to form a compound of formula B in which at least one of the dotted lines is absent.

In certain methods of the invention, the compound is a cyclic compound of formula II:

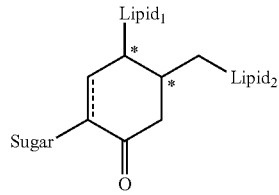

(II)

wherein Sugar is a C-linked glycoside; the dotted line ------ is absent or a bond, and $Lipid_1$ and $Lipid_2$ are each, independently selected from fats, waxes, sterols, fat-soluble vitamins, monoglycerides, diglycerides, phospholipids, and fatty acids.

In certain methods of the invention, the alkaline solution contains pyrrolidine. In certain methods of the invention, the carbohydrate-containing ketone is reacted with 2, 2.1, 2.2, 2.5, 3.0, 3.5, 4.0, 5.0, 7.0, 10.0 equivalents of aldehyde. In certain methods of the invention, the aldehyde is selected from butyraldehye or hexanal.

In certain methods of the invention, the compound is

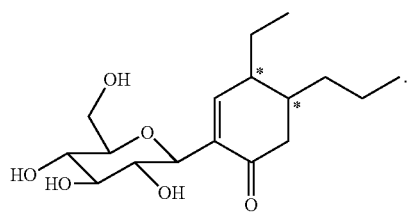

(2)

In certain methods of the invention, the compound is

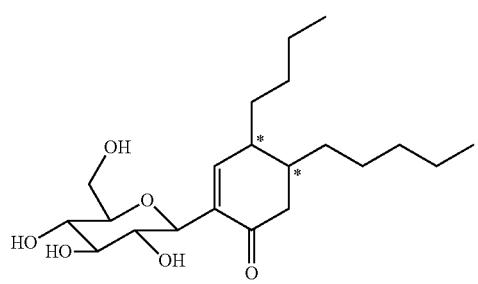

(3)

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. In addition, the materials, methods, and examples are illustrative only and are not intended to be limiting.

Other features and advantages of the invention will be apparent from the following detailed description and claims.

DETAILED DESCRIPTION OF THE INVENTION

Compounds

Figure 1:
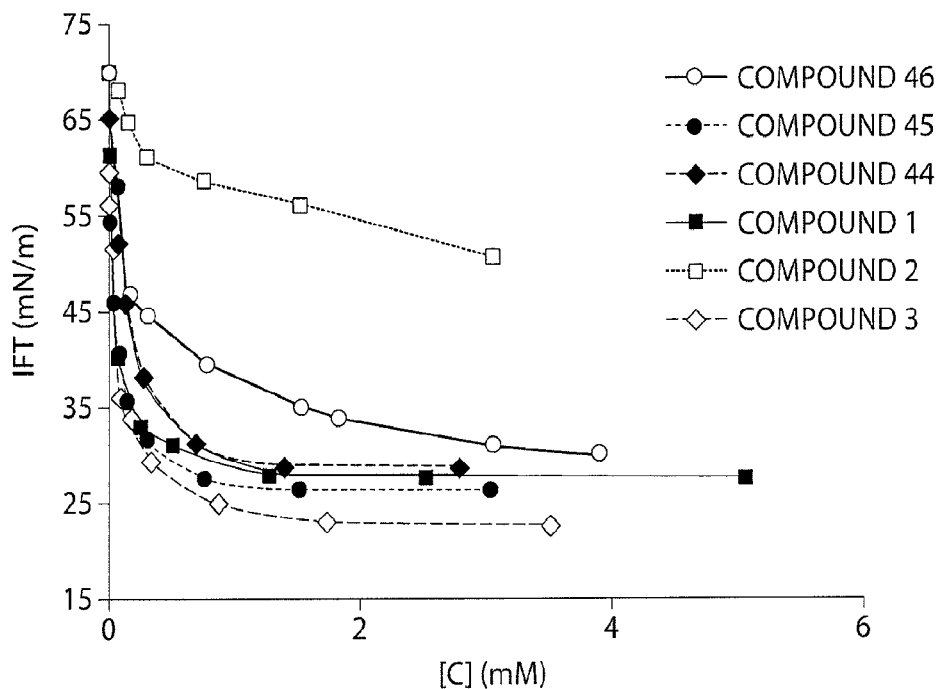
FIG. 1 is a graph that shows a comparison of CMC curves for selected compounds. The CMC is estimated by looking at the point of inflection on the respective curves.

The invention relates to novel linear and cyclic C-linked carbohydrate derivatives.

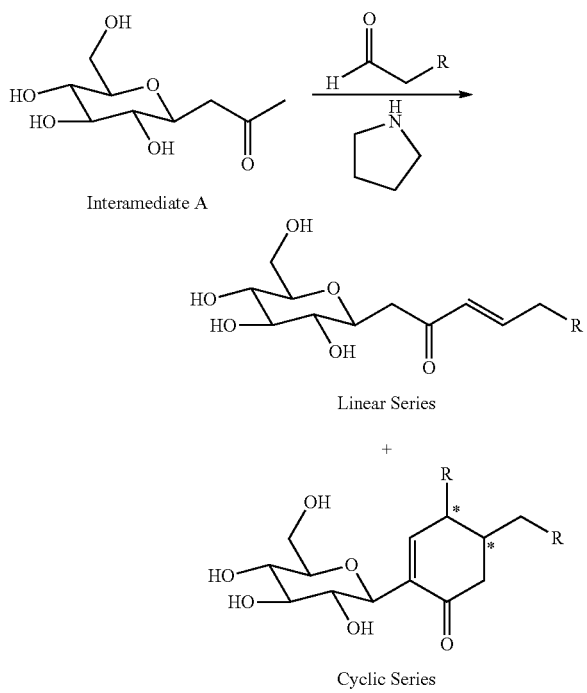

The compounds of the invention are the reaction products from the aldol condensation of aldehydes with Intermediate A. The cyclic series can be obtained as a mixture of isomers. Both series can be further functionalized or modified e.g., the enone can be reduced to a ketone. Both series have demonstrated unique surface activity properties in water.

Linear Series

The invention relates to novel linear, C-linked carbohydrate derivatives, to methods of using them and to processes for synthesizing them. The invention relates, in part, to a C-glycoside linked to an enone of formula A:

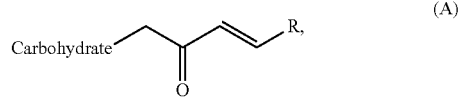

where "Carbohydrate" is a C-linked glycoside, and R is hydrogen or an alkyl chain that can be linear or branched, substituted or unsubstituted, can include one or more degrees of unsaturation, can include cyclic alkyl functionality, and can also include heteroatom substitution, including heterocycles.

In part, the invention also relates to novel enone-glycolipids.

For example, the invention relates to a novel class of amphiphilic compounds having a polar head group and a non-polar tail linked by an enone moiety. For example, a compound of the invention can include a carbohydrate moiety linked to a lipid via an enone, according to formula (I):

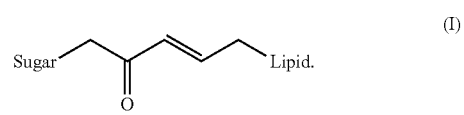

The enone-linked compounds according to the invention can be generated by a two-step process.

First, a C-glycosylic ketone intermediate,

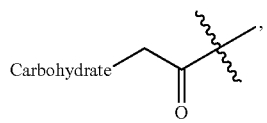

can be generated by a Knoevenagel-type condensation reaction between a carbohydrate and a 1,3-diketone in aqueous media. See, e.g., Rodrigues at al., Chem. Commun. (2000) 2049-2050; Riemann et al., Aust. J. Chem., 55 (2002) 147-154; and Hersant et al., Carbohydrate Research 339 (2004) 741-745.

The carbohydrate can be a mono- or polysaccharide or their derivatives, such as glucose, xylose, lyxose, mannose, maltose, cellobiose, galactose, glycosidic derivatives thereof, etc. For example, the carbohydrate reactant can be a biomass fraction.

Suitable diketone reactants include, for example, acetylacetone or ethylacetoacetate.

Scheme I illustrates an example of the reaction involving glucose as the carbohydrate:

Scheme I:

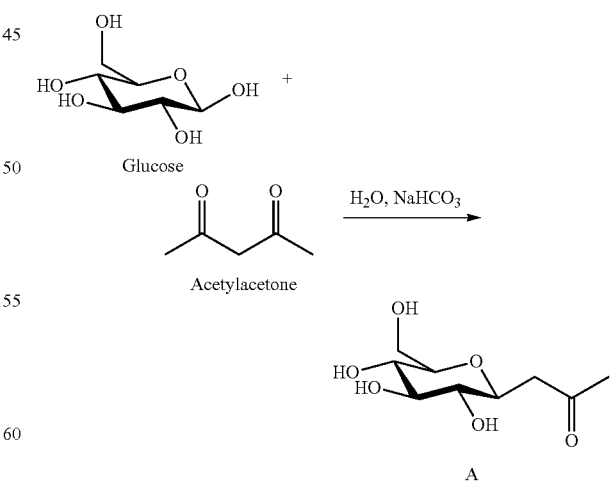

In the second step, the C-glycosylic ketone (intermediate A) is subjected to an aldol condensation reaction with an aldehyde, RC(O)H. The result is an enone alpha to a C-glycoside, a compound according to formula A:

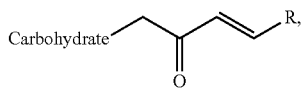
(A)

The aldehyde used in the second step of the reaction can be, for example, straight chain or branched alkyl, and can contain unsaturation. In some embodiments, the alkyl chain can include substituents or heteroatoms in place of a carbon atom.

Further, the condensation reaction may be performed with a ketone in place of an aldehyde.

Preferably, the aldehyde or ketone moiety is non-polar, e.g., as in a lipid, such that the resultant glycosylic enone conjugate is amphiphilic. For example, compounds of formula I can be generated in this fashion:

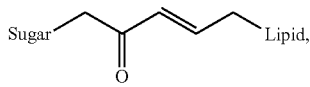
(I)

The lipid can be, for example, any lipid, such as a fatty acid. The carbon chain is typically between four to 24 carbons long, may be saturated or unsaturated, and may be attached to functional groups containing, for example, oxygen, halogen, nitrogen and/or sulfur. Where a double bond exists (other than that already specified in the formulae), there is the possibility of either a cis (Z) or trans (E) geometric isomerism, which significantly affects the molecule's molecular configuration. Cis-double bonds cause the fatty acid chain to bend, an effect that is more pronounced the more double bonds there are in a chain.

One example of the reaction between a C-glycosylic ketone and a hydrophobic lipid is shown below in Scheme II Scheme II:

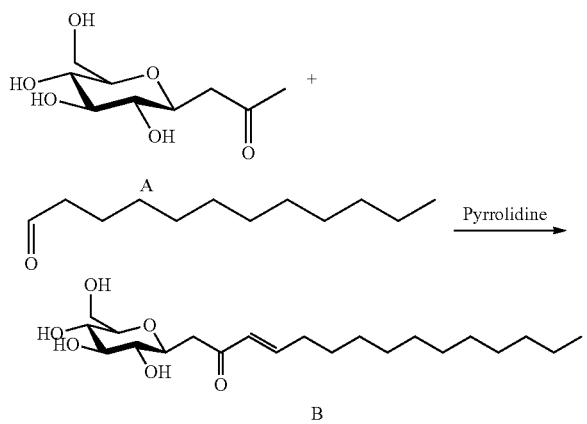

The hydroxyl groups of the mono- or polysaccharide of the C-glycosylic enone obtained via the methods described above can further be subjected to derivatization reactions, such as those described in Luders, H; Balzer, D., ed. *Nonionic Surfactants: Alkyl Polyglucosides, Ch.* 4. Marcel Dekker Inc., New York, 2000. ISBN 0-8247-9390-0. The specific derivatization can be selected to control the HLB of the C-glycosylic enone. Examples of functional groups, which can replace one or more hydroxyl groups of the sugar moiety, are listed below.

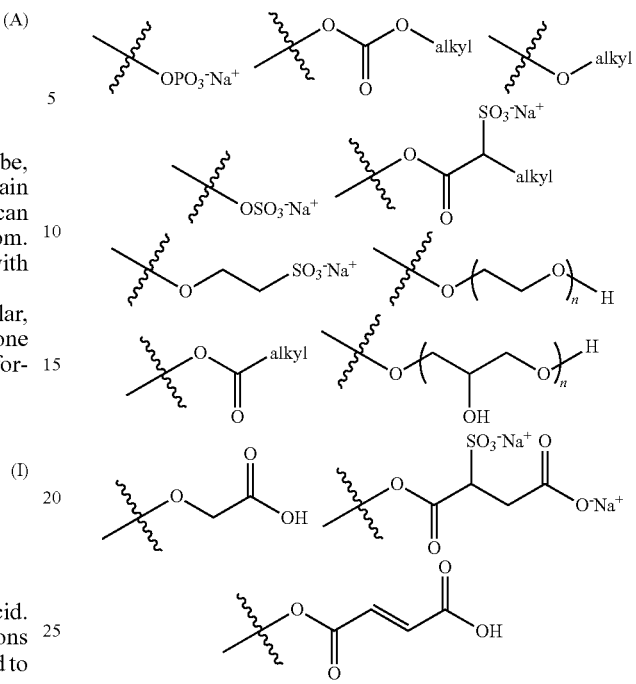

Without wishing to be bound by theory, it is thought that the enone moiety bestows the amphiphile with a functionality that will have unique properties as compared to traditional carbohydrate-based amphiphiles, such as those described in, e.g., Bisht et al. *Carb. Res.* 2008, 343, 1399-1406; U.S. Pat. Nos. 7,049,300; 7,358,346 and PCT publications WO 02/051803; WO 02/0518028. For example, the conjugated $sp^2$ nature of the enone may offer a degree of extended rigidity to the center of the molecule that potentially affects self-assembly behavior of the molecule. Additionally, the enone can participate in Michael-additions, E-Z conformational flipping, and photoisomerization, elements that may make the behavior of these molecules tunable under appropriate conditions.

Further, the enone may also participate in free radical polymerization reactions for use in developing novel compositions.

Thus the enone-glycosides (e.g., enone glycolipids) of the invention can be made by a two step synthesis, using only water as solvent, and can incorporate renewable, readily available substrates.

Cyclic Series

The invention relates to novel, cyclic C-linked carbohydrate derivatives, to methods of using them and to processes for synthesizing them. The invention relates, in part, to a compound of formula B:

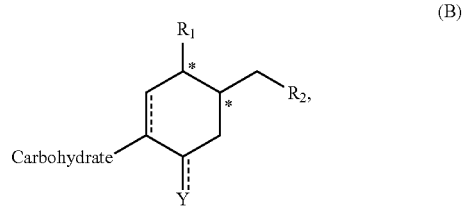
(B)

wherein "Carbohydrate" is a C-linked glycoside, each of $R_1$, and $R_2$, independently, is hydrogen, linear alkyl, branched alkyl, substituted linear alkyl, substituted branched alkyl, cycloalkyl, or substituted cycloalkyl, each of the two dotted lines ------, independently, is absent or a bond, and Y is O or $OR_8$, in which $R_8$ is hydrogen or $C_1$-$C_{10}$ alkyl.

In part, the invention relates to a compound of formula B1:

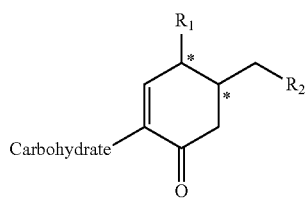

(B1)

wherein Carbohydrate, $R_1$, and $R_2$ are as defined herein.

In part, the invention relates to a compound having a formula selected from:

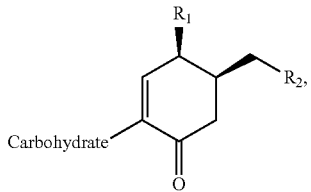

(B2)

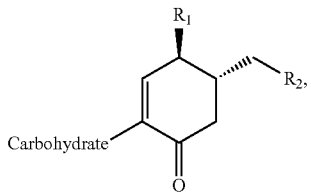

(B3)

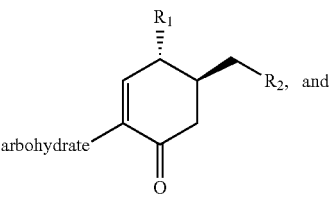

(B4)

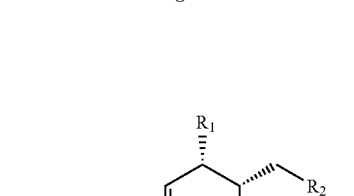

(B5)

wherein Carbohydrate, $R_1$, and $R_2$ are as defined herein.

In part, the invention relates to a compound having the formula:

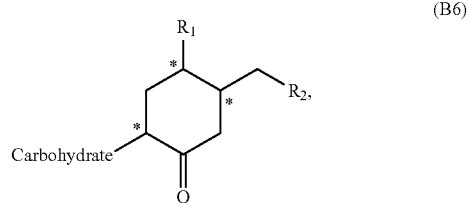

(B6)

wherein Carbohydrate, $R_1$, and $R_2$ are as defined herein.

In part, the invention relates to a compound having a formula selected from:

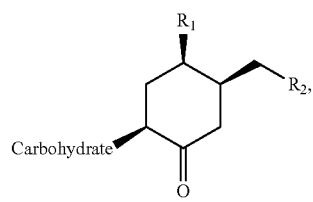

(B7)

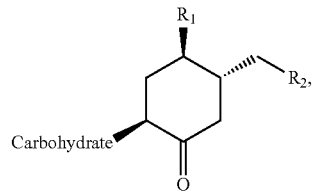

(B8)

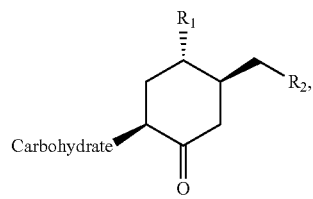

(B9)

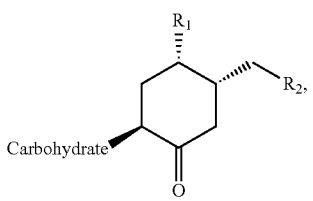

(B10)

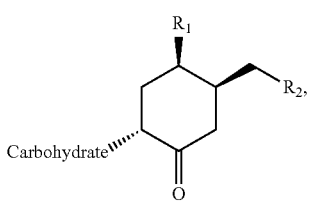

(B11)

-continued

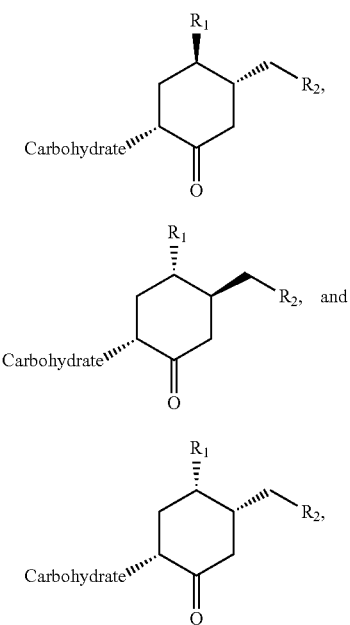

wherein Carbohydrate, $R_1$, and $R_2$ are as defined herein.

In part, the invention relates to a compound having the formula:

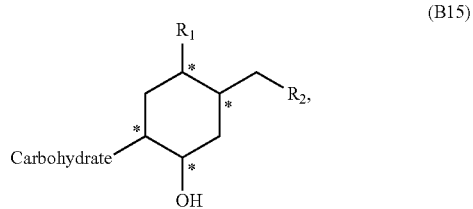

wherein Carbohydrate, $R_1$, and $R_2$ are as defined herein. Similar to the compounds of formulae B7 through B14, the compound of formula B15 includes all of its chiral isomers.

In part, the invention relates to a compound having the formula:

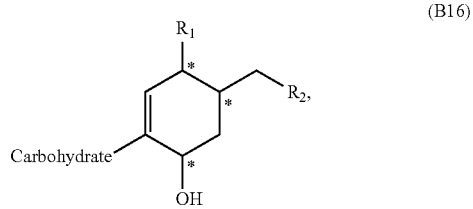

wherein Carbohydrate, $R_1$, and $R_2$ are as defined herein. Similarly, the compound of formula (B16) includes all of its chiral isomers.

In some compounds, $R_1$ and $R_2$ are the same. In some compounds, $R_1$ and $R_2$ are different.

In some compounds, $R_1$ and $R_2$ are each independently selected from saturated or unsaturated alkyl. In some compounds, $R_1$ is alkyl having one degree of unsaturation. In some compounds, $R_2$ is alkyl having one degree of unsaturation.

In some compounds, $R_1$ and $R_2$ are each an aliphatic chain of a fatty acid. In some compounds $R_1$ is an aliphatic chain of a fatty acid. In some compounds, $R_2$ is an aliphatic chain of a fatty acid.

In some compounds, $R_1$ and $R_2$ are each an alkyl group having 2, 3, 4, 5, 6, 7, 8, 9, or 10 carbon atoms. In some compounds, $R_1$ is an alkyl group having 2, 3, 4, 5, 6, 7, 8, 9 or 10 carbon atoms. In some compounds, $R_2$ is an alkyl group having 2, 3, 4, 5, 6, 7, 8, 9, or 10 carbon atoms.

In some compounds, $R_1$ and $R_2$ are each an alkyl group having from 2, 3, 4, 5, or 6 carbon atoms. In some compounds, $R_1$ is an alkyl group having 2, 3, 4, 5, or 6 carbon atoms. In some compounds, $R_2$ is an alkyl group having 2, 3, 4, 5, or 6 carbon atoms.

In some compounds, Carbohydrate is a mono- or polysaccharide. In some compounds, Carbohydrate is selected from glucose, xylose, lyxose, mannose, maltose, cellobiose, and galactose. In some compounds, Carbohydrate is glucose.

In some compounds, Carbohydrate is derived from a biomass fraction. The term "biomass" refers to biological material derived from living or recently living organisms e.g., wood, plant matter.

In some compounds, the dotted line is absent. When the dotted line is absent, the 6-membered ring is completely saturated. In some compounds, the dotted line is a bond. When the dotted line is a bond, the 6-membered ring has a double-bond. The 6-membered ring has an alpha, beta unsaturated carbonyl moiety.

The invention relates to a compound of formula II:

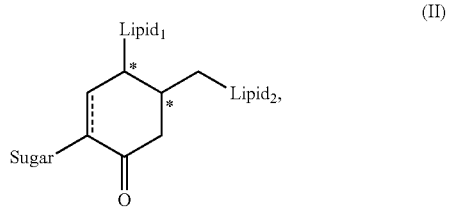

wherein Sugar is a C-linked glycoside; the dotted line is absent or a bond, and Lipid$_1$ and Lipid$_2$ are each, independently selected from fats, waxes, sterols, fat-soluble vitamins, monoglycerides, diglycerides, phospholipids, and fatty acids.

In some compounds, Lipid$_1$ and Lipid$_2$ are the same. In some compounds, Lipid$_1$ and Lipid$_2$ are different.

In some compounds, Lipid$_1$ and Lipid$_2$ are each an aliphatic chain of a fatty acid. In some compounds, Lipid$_1$ is an aliphatic chain of a fatty acid. In some compounds, Lipid$_2$ is an aliphatic chain of a fatty acid.

In some compounds, the aliphatic chain of a fatty acid has 2, 3, 4, 5, 6, 7, 8, 9 or 10 carbon atoms. In some compounds, the aliphatic chain of a fatty acid has 2, 3, 4, 5, or 6 carbon atoms.

In some compounds, Sugar is a mono- or polysaccharide. In some compounds, Sugar is selected from glucose, xylose, lyxose, mannose, maltose, cellobiose, and galactose. In some compounds, Sugar is glucose.

In some compounds, Sugar is derived from a biomass fraction.

In some compounds, Sugar is a monosaccharide and Lipid$_1$ and Lipid$_2$ are each an aliphatic chain of a fatty acid. In some compounds, the Sugar is a monosaccharide and Lipid$_1$ is an aliphatic chain of a fatty acid. In some compounds, the Sugar is a monosaccharide and Lipid$_2$ is an aliphatic chain of a fatty acid.

The invention relates to a compound selected from:
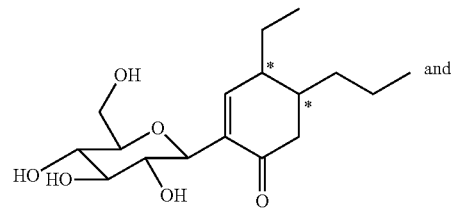
(2)
and
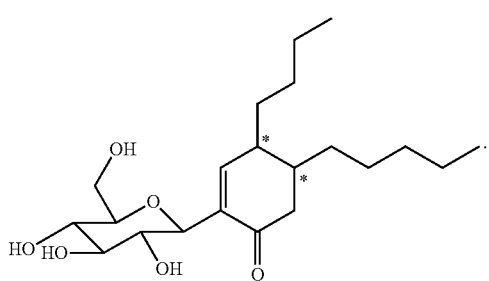
(3)
The invention includes a compound selected from:
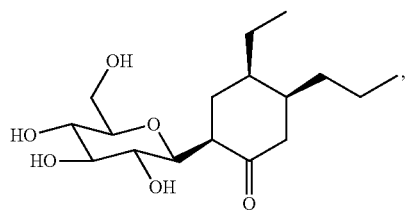
(4)
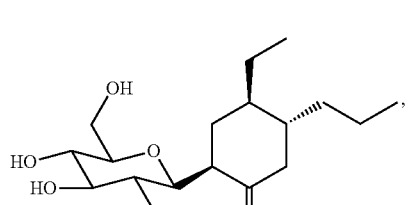
(5)
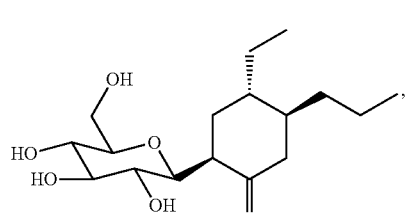
(6)
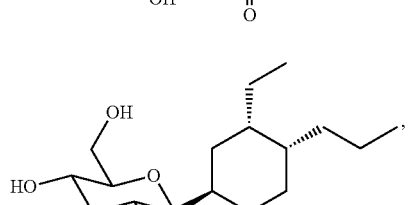
(7)
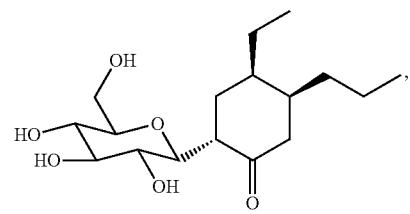
(8)
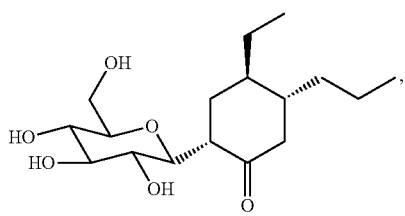
(9)
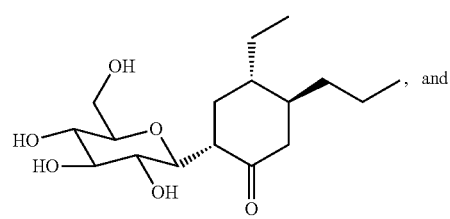
(10)
, and
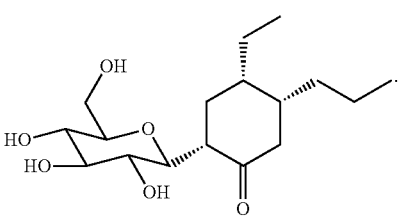
(11)
The invention also relates to a compound selected from:
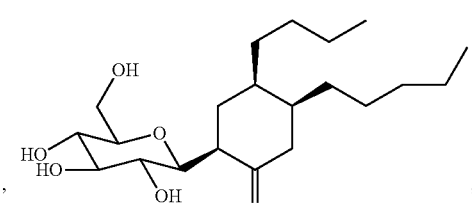
(12)
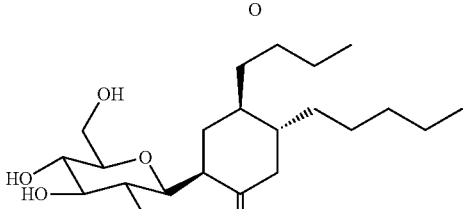
(13)
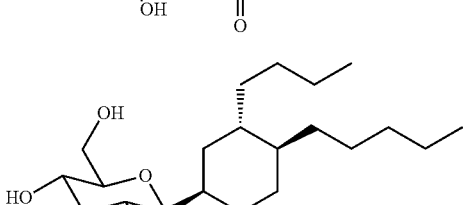
(14)

(15)
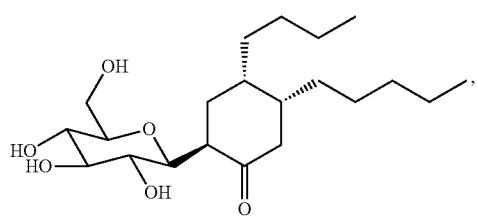
(16)
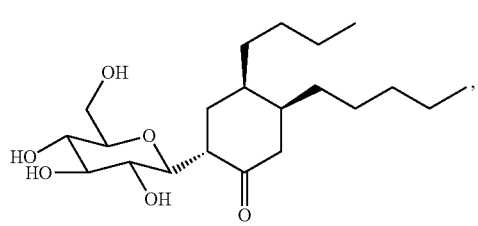
(17)
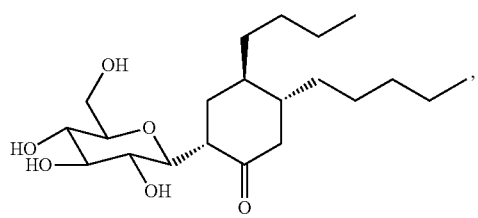
(18)
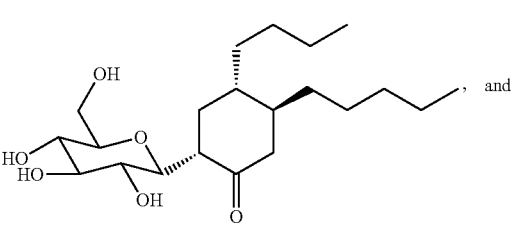,  and
(19)
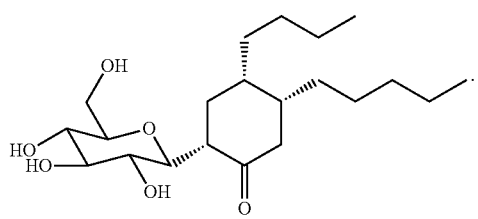
The invention relates to a compound selected from:
(20)
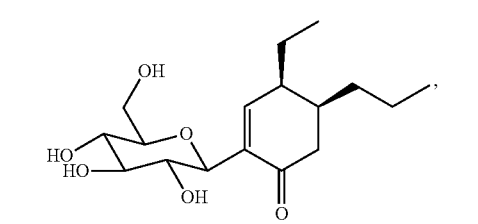
(21)
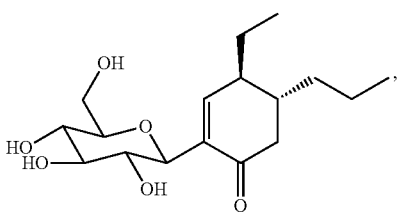
(22)
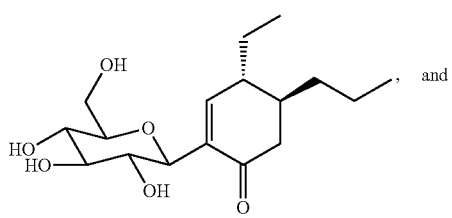,  and
(23)
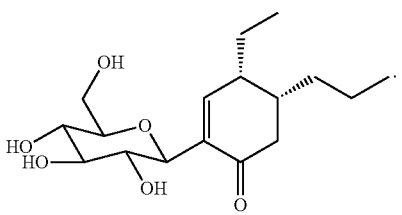
The invention relates to a compound selected from:
(24)
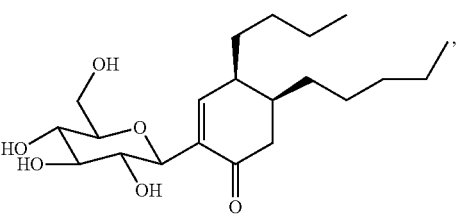
(25)
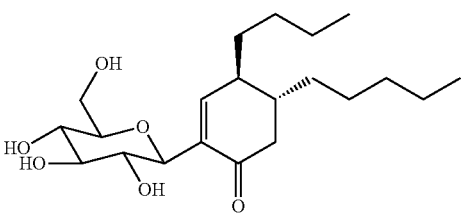
(26)
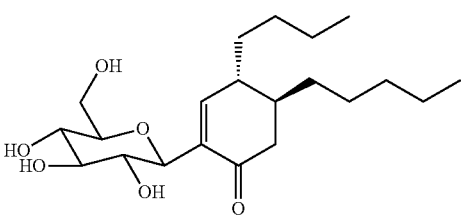
(27)
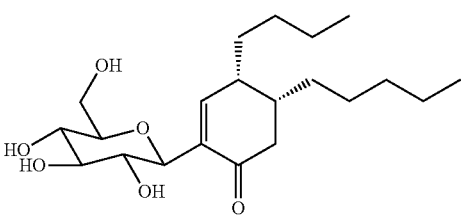

(28) 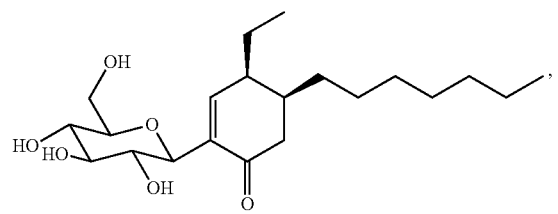
(29) 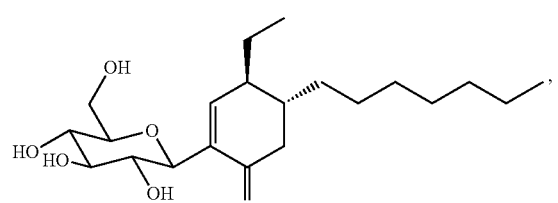
(30) 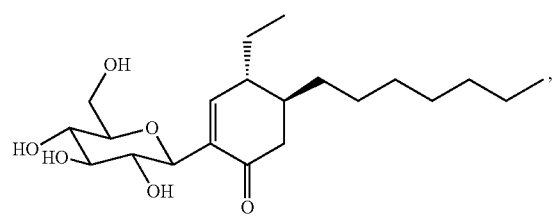
(31) 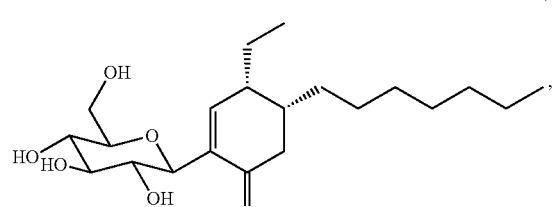
(32) 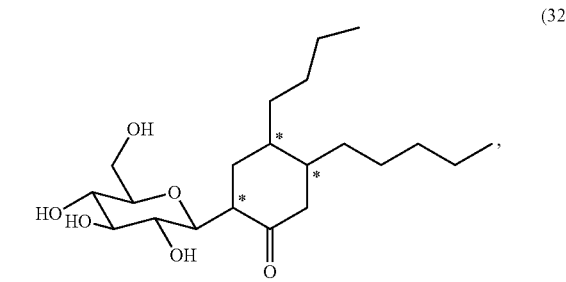
(33) 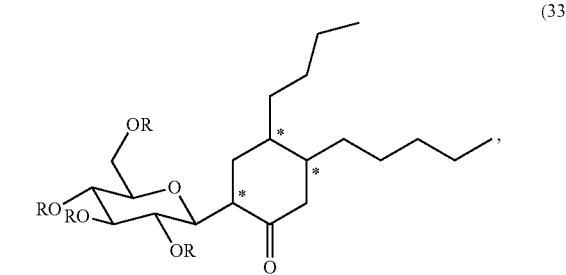
(34) 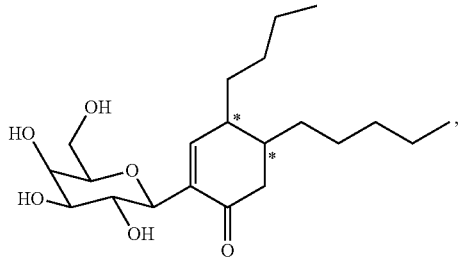
(35) 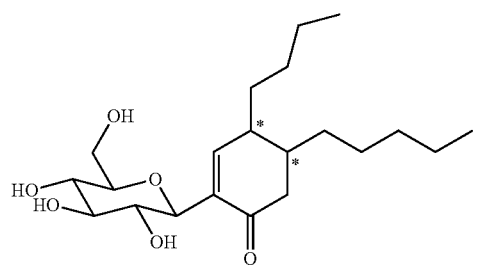
(36) 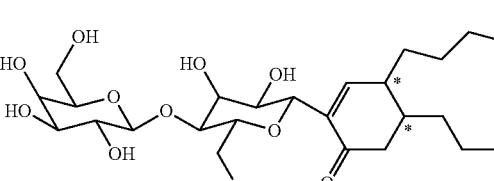
(37) 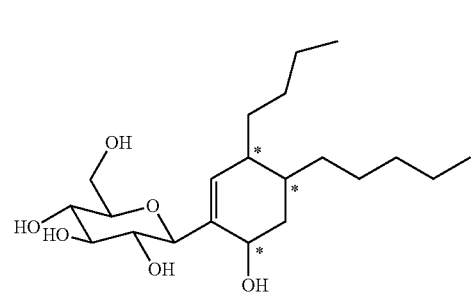
(38) 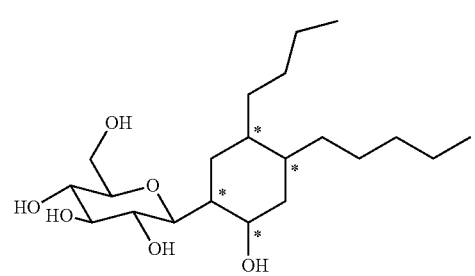
(39) 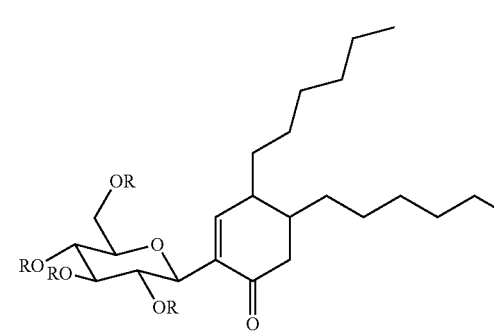

-continued

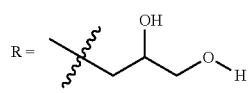

in which each R independently is H or SO$_3$Na, (40)

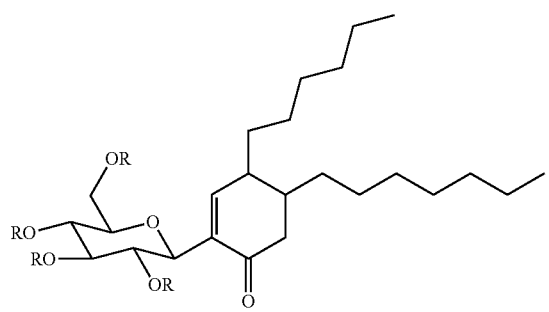

in which each R independently is H or —(CH$_2$CH$_2$O)$_n$—H with n being 1, 2, or 3, (41)

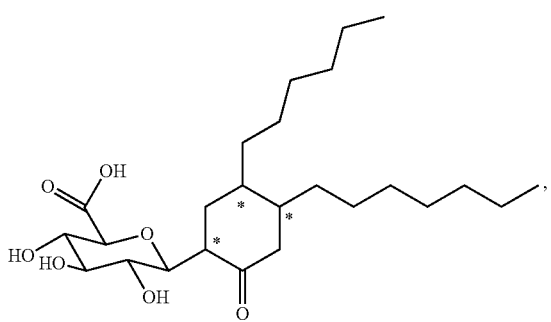

(42)

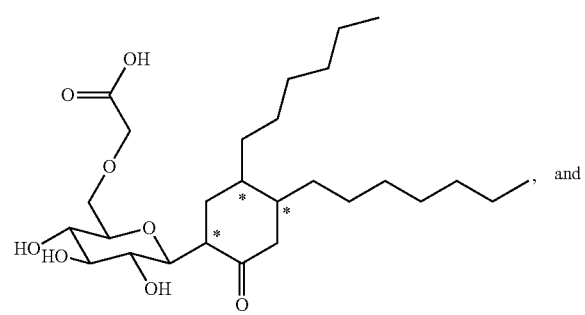
, and (43)

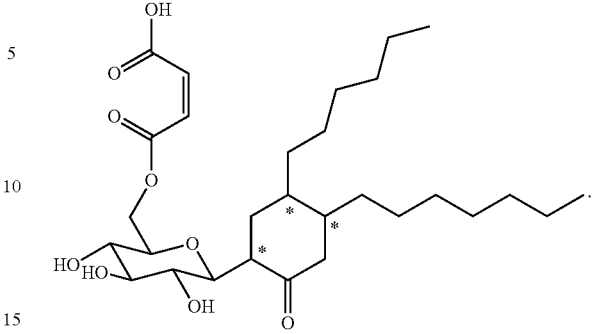

The invention also relates to a compound selected from:

(44)

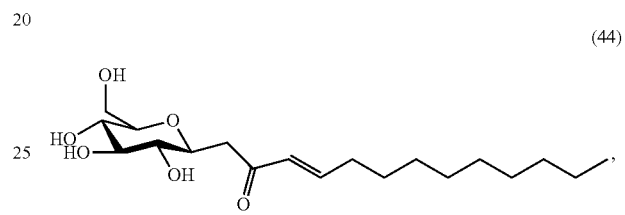

(45)

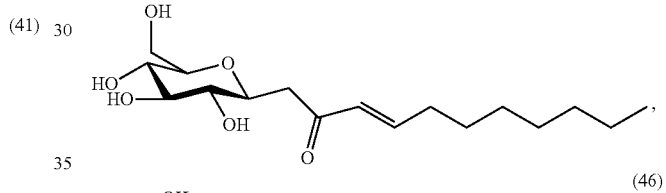

(46)

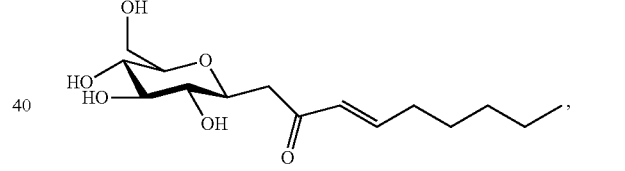

(47)

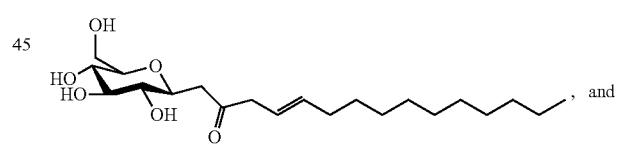
, and (48)

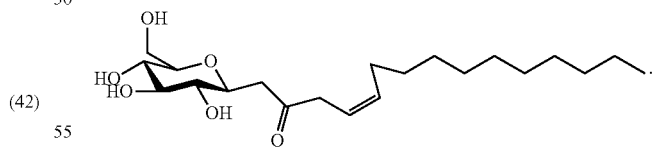

The invention relates to a composition comprising a compound described herein. The composition may further include a surfactant such as an anionic surfactant.

Uses

Compounds of the invention are amphiphilic, having both hydrophobic and hydrophilic components. Such molecules have a broad range of applications as surface active agents (i.e., surfactants) and/or polymer precursors.

To characterize the behavior of the compounds of this invention as surfactants, surface tension can be plotted as a function of concentration and critical micelle concentrations (CMCs) of these surfactants can be calculated. In addition, the hydrophobic-lipophilic balance (HLB) of a surfactant can be calculated according to Griffin's Method. See e.g., Pasquali, R. C.; Taurozzi, M. P.; Bregni, C. *Int. J. Pharm.* 2008, 356, 44. Further, foaming properties of a surfactant can be evaluated using the Ross-Miles foam test according to the known ASTM protocol, i.e., ASTM Standard D1173, 2007, ASTM International, DOI: 10.1520/D1173-07.

Owing to their amphiphilic nature, the compounds of the invention have potential use in a variety of applications, such as, for example, surfactants; emulsifiers; lubricants; antibacterial or disinfecting agents; bioactive therapeutic agents; polymer precursors for chiral solid phase media; polymer precursors for amphiphilic membranes; phase-transfer catalysts; coagulants; DNA, drug, or macromolecule transvection vectors; antigen presenting nanoparticles; controlled release drug delivery components; and various other functional nano-objects.

For example, the compounds of the invention could be used in formulations for use as detergents for personal care or household use, use in formulation for drug delivery, and/or use in formulation for surfactant based brown field remediation.

Some compounds of the invention may be used, for example, as polymer precursors. Reaction of the C-glycosidic ketone intermediate (A) with formaldehyde (R=H) will result in an unsubstituted enone of formula A, which is a very reactive polymerizing functionality. Such molecules could substitute for methyl vinyl ketones. The resulting polymers will be chiral, biodegradable, and amphiphilic, as well as made from renewable materials.

Synthesis

Linear Series

In part, the invention relates to a method of synthesizing an enone glycoside of formula A, wherein the method includes:

(a) reacting a carbohydrate with a 1,3-diketone in water in a mildly alkaline aqueous solution to form a C-glycoside intermediate,

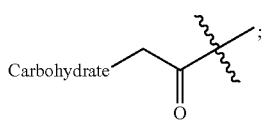

and (b) reacting the C-glycoside intermediate with an aldehyde in the presence of a catalyst to form an enone glycoside having the formula:

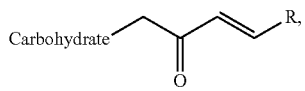

where "Carbohydrate" is a C-linked glycoside, and R is hydrogen or an alkyl chain that can be linear or branched, substituted or unsubstituted, can include one or more degrees of unsaturation, can include cyclic alkyl functionality, and can also include heteroatom substitution, including heterocycles.

For example, the carbohydrate used in the synthesis of the invention can be a mono- or poly saccharide. In one synthesis, the carbohydrate is glucose.

The aqueous solution in step (a) can be made alkaline by any number of reagents, including, for example, sodium bicarbonate.

The aldehyde used in the method of the invention can be non-polar. For example, the aldehyde can be a lipid and can include various degrees of unsaturation. The unsaturated compounds can include double bonds in the cis (Z)- or trans (E)-configuration.

The catalyst in step (b) of the method of the invention can be, for example, pyrrolidine.

In part, the invention relates to the synthesis of an enone glycolipid compound of formula I:

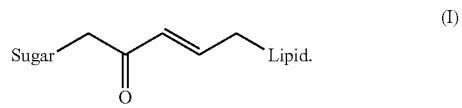

The production of enone-glycolipid amphiphiles of the invention will ideally require minimum use of hazardous materials, almost no solvent outside of water, and will maximally incorporate renewable feedstocks.

Step (a) is thought to proceed to near quantitative yields, and the workup can include ion-exchange to remove inorganic impurities, and/or an extraction step to give the desired purity of the c-glycoside intermediate. After the second step (b) the catalyst can be removed, such as, for example, by converting a base to a salt and subsequent precipitation. For example, the catalyst can then be regenerated and reused. Any remaining impurities can then be removed by either distillation or by two phase extraction.

Cyclic Series

In part, the invention relates to a method of synthesizing a cyclic compound of formula B:

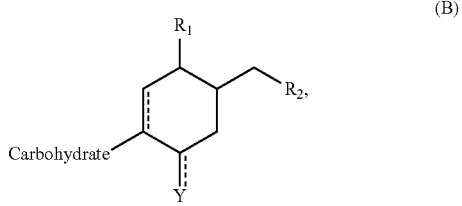

wherein Carbohydrate is a C-linked glycoside, each of $R_1$ and $R_2$, independently, is hydrogen, linear alkyl, branched alkyl, substituted linear alkyl, substituted branched alkyl, cycloalkyl, or substituted cycloalkyl, each of the two dotted lines ------, independently, is absent or a bond, and Y is O or $OR_a$, in which $R_a$ is hydrogen or $C_1$-$C_{10}$ alkyl. The method comprising: reacting a carbohydrate-containing ketone with excess aldehyde in an alkaline solution to form a compound of formula B'

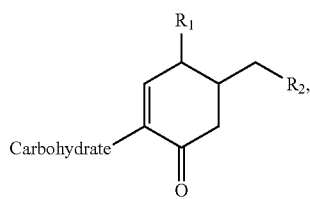

which is then reduced to form a compound of formula B. The scheme below shows an example:

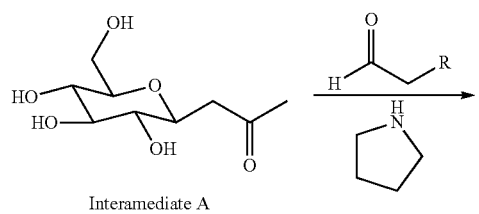

In some methods, the Carbohydrate is a mono- or polysaccharide.

In some methods, the Carbohydrate is selected from glucose, xylose, lyxose, mannose, maltose, cellobiose, and galactose.

In some methods, the Carbohydrate is glucose.

In some methods, the Carbohydrate is derived from a biomass fraction.

In some methods, $R_1$ and $R_2$ are each lipids. In some methods, $R_1$ is a lipid. In some compounds, $R_2$ is a lipid.

In some methods, $R_1$ and $R_2$ are each an aliphatic chain of a fatty acid. In some compounds, $R_1$ is an aliphatic chain of a fatty acid. In some compounds, $R_2$ is an aliphatic chain of a fatty acid.

In some methods, $R_1$ and $R_2$ are each alkyl having 2, 3, 4, 5, 6, 7, 8, 9, or 10 carbon atoms. In some compounds, $R_1$ is an alkyl having 2, 3, 4, 5, 6, 7, 8, 9, or 10 carbon atoms. In some compounds, $R_2$ is an alkyl having 2, 3, 4, 5, 6, 7, 8, 9, or 10 carbon atoms.

In some methods, $R_1$ and $R_2$ are each alkyl having 2, 3, 4, 5, or 6 carbon atoms. In some compounds, $R_1$ is an alkyl having 2, 3, 4, 5, or 6 carbon atoms. In some compounds, $R_2$ is an alkyl having 2, 3, 4, 5, or 6 carbon atoms.

In some methods, the enone double bond is reduced in the presence of hydrogen gas and a palladium catalyst.

In some methods, the compound is a cyclic compound of formula II:

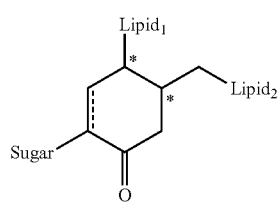

wherein Sugar is a C-linked glycoside; the dotted line ------ is absent or a bond, and $Lipid_1$ and $Lipid_2$ are each, independently selected from fats, waxes, sterols, fat-soluble vitamins, monoglycerides, diglycerides, phospholipids, and fatty acids.

In some methods, the alkaline solution contains pyrrolidine.

In some methods, the carbohydrate-containing ketone is reacted with 2, 2.1, 2.2., 2.5, 3.0, 3.5, 4.0, 5.0, 7.0, 10.0 equivalents of aldehyde. In some methods, the aldehyde is selected from butyraldehye or hexanal.

In some methods, the compound is

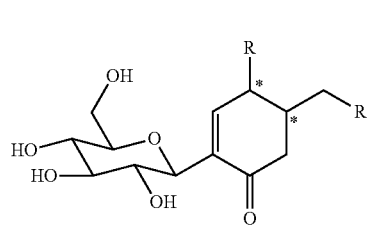

In some methods, the compound is

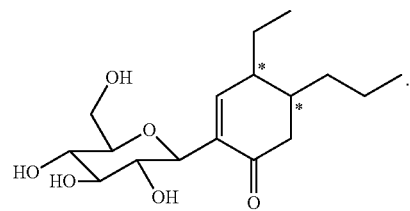

In some methods, the sugar moiety is further modified. Schemes III, IV, and V below are shown as examples.

Scheme III

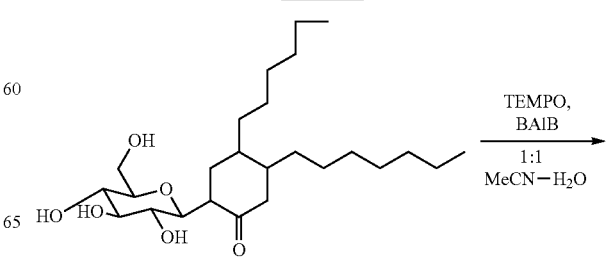

-continued

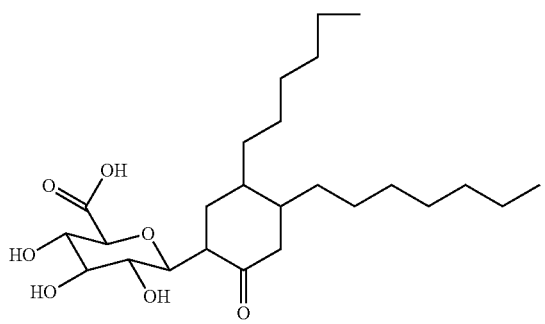

As shown in Scheme III above, C-glycoside (1.0 equivalent), [bis(acetoxy)iodo]benzene (2.2 equivalents), and 2,2,6,6-tetramethypiperidine-1-oxyl (0.2 equivalents) can be combined and taken up in a 1:1 solution of acetonitrile and water. After stirring for three hours, the reaction can then be acidified with 1N HCl, and either extracted with 1-butanol, or concentrated and extracted with methanol, leaving behind any inorganic residue. The corresponding organic layer can then be concentrated to obtain a mixture enriched with the desired carboxyl derivative. More procedural details can be found for example in *J. Org. Chem.* 1999, 64, 293-295.

Scheme IV

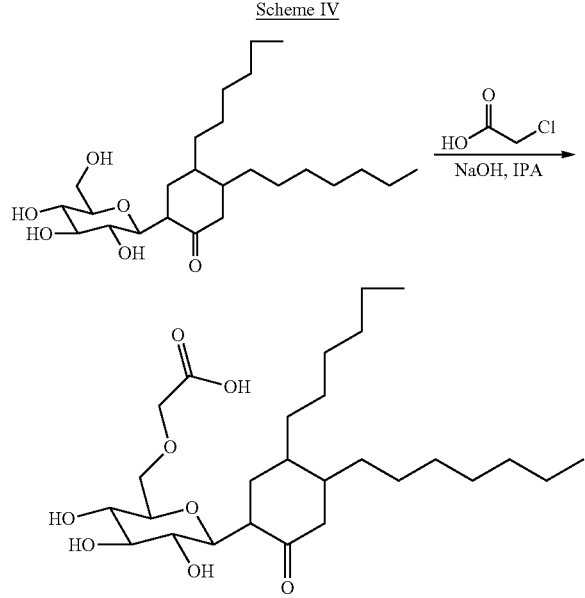

As shown in Scheme IV, C-glycoside (1.0 equivalent) can be dissolved in isopropyl alcohol and sodium hydroxide (7.5 equivalents) can be added. After 40 minutes of stirring, chloroacetic acid can be added (5.0 equivalents) in five portions at intervals of 5 minutes. The reaction can then be heated to 40° C. for 3 hours. The reaction can then be acidified with 1N HCl, and either extracted with 1-butanol, or concentrated and extracted with methanol, leaving behind any inorganic residue. The corresponding organic layer can then be concentrated to obtain a mixture enriched with the desired carboxyl derivative. More procedural details can be found for example in *Carb. Res.* 2010, 345, 120

Scheme V

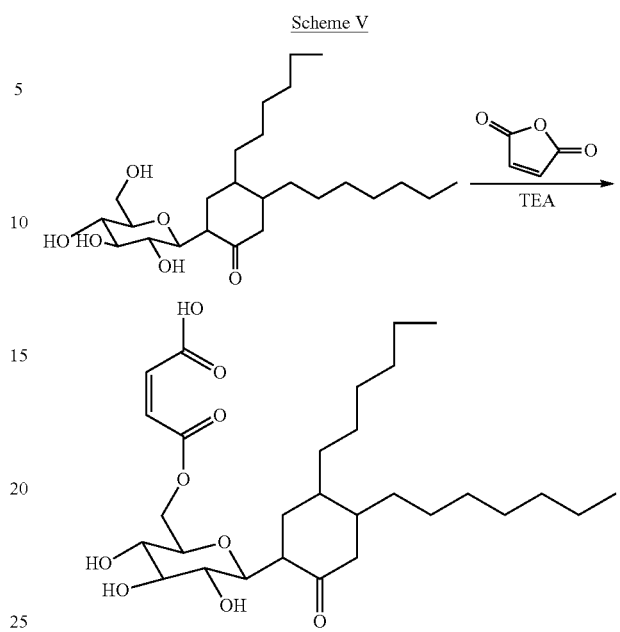

As shown in Scheme V, 1.1 equivalents of triethylamine can be added to 1.0 equivalent of C-glycoside and 1.0 equivalent of maleic anhydride at room temperature and the slurry can be heated to 50° C. with stirring for 1 hour. The reaction mixture can then be dissolved in water, and acidified with 1N HCl. This aqueous layer can then be either extracted with 1-butanol or concentrated and extracted with methanol to leave behind any inorganic residue. The corresponding organic phase can then be concentrated resulting in a mixture enriched with desired carboxyl derivative. See, e.g., *J. Med. Chem.* 1986, 29, 1868-1871

Examples of functional groups, which can replace one or more hydroxyl groups of the sugar moiety, are listed below.

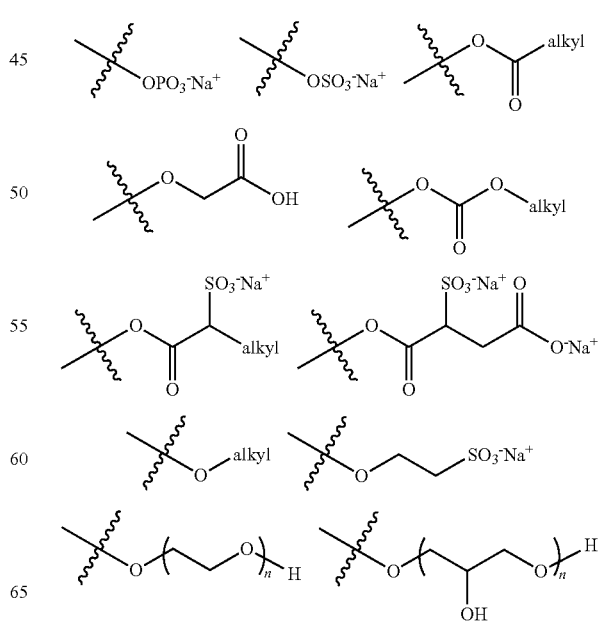

-continued

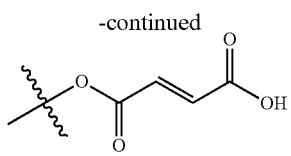

All forms of the compounds of the instant invention are contemplated, either in admixture or in pure or substantially pure form.

In the present specification, the structural formula of the compound represents a certain isomer for convenience in some cases, but the present invention includes all isomers, such as geometrical isomers, optical isomers based on an asymmetrical carbon, stereoisomers, tautomers, and the like. In addition, a crystal polymorphism may be present for the compounds represented by the formula. It is noted that any crystal form, crystal form mixture, or anhydride or hydrate thereof is included in the scope of the present invention.

"Isomerism" means compounds that have identical molecular formulae but differ in the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images of each other are termed "enantiomers" or sometimes optical isomers. A mixture containing equal amounts of individual enantiomeric forms of opposite chirality is termed a "racemic mixture".

A carbon atom bonded to four nonidentical substituents is termed a "chiral center."

"Chiral isomer" means a compound with at least one chiral center. Compounds with more than one chiral center may exist either as an individual diastereomer or as a mixture of diastereomers, termed "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the *Sequence Rule* of Calm, Ingold and Prelog. (Cahn et al., *Angew. Chem. Inter. Edit.* 1966, 5, 385; errata 511; Cahn et al., *Angew. Chem.* 1966, 78, 413; Calm and Ingold, *J. Chem. Soc.* 1951 (London), 612; Cahn et al., *Experientia* 1956, 12, 81; Cahn, *J. Chem. Educ.* 1964, 41, 116). In some formulae of the present application, one or more chiral centers are identified by an asterisk placed next to the chiral carbon. In other formulae, no chiral center is identified, but the chiral isomers are nonetheless covered by these formulae.

"Geometric isomer" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Some compounds of the present invention can exist in a tautomeric form which is also intended to be encompassed within the scope of the present invention. "Tautomers" refers to compounds whose structures differ markedly in arrangement of atoms, but which exist in easy and rapid equilibrium. It is to be understood that the compounds of the invention may be depicted as different tautomers. It should also be understood that when compounds have tautomeric forms, all tautomeric forms are intended to be within the scope of the invention, and the naming of the compounds does not exclude any tautomeric form. Further, even though one tautomer may be described, the present invention includes all tautomers of the present compounds.

As used herein, the term "salt" can include acid addition salts including hydrochlorides, hydrobromides, phosphates, sulfates, hydrogen sulfates, alkylsulfonates, arylsulfonates, acetates, benzoates, citrates, maleates, fumarates, succinates, lactates, and tartrates; alkali metal cations such as $Na^+$, $K^+$, $Li^+$, alkali earth metal salts such as $Mg^{2+}$ or $Ca^{2+}$, or organic amine salts.

The term "mixing" means combining, blending, stirring, shaking, swirling or agitating. The term "stirring" means mixing, shaking, agitating, or swirling. The term "agitating" means mixing, shaking, stirring, or swirling.

Unless otherwise indicated, the disclosure is not limited to specific procedures, starting materials, or the like, as such may vary. It is also to be understood that the terminology used herein is for the purpose of describing particular embodiments only and is not intended to be limiting.

As used herein, the singular forms "a," "an," and "the" include plural referents unless the context clearly dictates otherwise. Thus, for example, reference to "a reactant" includes not only a single reactant but also a combination or mixture of two or more different reactant, reference to "a substituent" includes a single substituent as well as two or more substituents, and the like.

As used herein, the phrases "for example," "for instance," "such as," or "including" are meant to introduce examples that further clarify more general subject matter. These examples are provided only as an aid for understanding the disclosure, and are not meant to be limiting in any fashion. Furthermore as used herein, the terms "may," "optional," "optionally," or "may optionally" mean that the subsequently described circumstance may or may not occur, so that the description includes instances where the circumstance occurs and instances where it does not. For example, the phrase "optionally present" means that an object may or may not be present, and, thus, the description includes instances wherein the object is present and instances wherein the object is not present.

As used herein, the phrase "having the formula" or "having the structure" is not intended to be limiting and is used in the same way that the term "comprising" is commonly used.

The term "alkyl" as used herein refers to a branched or unbranched saturated or unsaturated hydrocarbon group typically although not necessarily containing 1 to about 24 carbon atoms, such as methyl, ethyl, n-propyl, isopropyl, n-butyl, isobutyl, t-butyl, octyl, decyl, and the like. Generally, although not necessarily, alkyl groups in the lipids described herein may contain 4 to about 28 carbon atoms, and such groups may contain 10 to about 28 carbon atoms. "Substituted alkyl" refers to alkyl substituted with one or more substituent groups, and the terms "heteroatom-containing alkyl" and "heteroalkyl" refer to an alkyl group in which at least one carbon atom is replaced with a heteroatom such as O, S, Se, N, or P.

As used herein, the term "cycloalkyl" is intended to include saturated or unsaturated nonaromatic hydrocarbon rings having 3 to 30 carbon atoms. The term "$C_3$-$C_8$ cycloalkyl" thus refers to a cycloalkyl having 3, 4, 5, 6, 7, or 8 carbon atoms in its ring structure. In one embodiment, a cycloalkyl group has five or six carbons in the ring structure, such as cyclopentyl, cyclopentenyl, cyclohexyl and the like. "Substituted cycloalkyl" refers to cycloalkyl substituted with one or more substituent groups, and the terms "heteroatom-containing cycloalkyl" and "heterocycloalkyl" refer to an cycloalkyl ring in which at least one carbon atom is replaced with a heteroatom.

"Aryl" includes groups with aromaticity, including "conjugated" or multicyclic, systems with at least one aromatic ring. Examples include phenyl, benzyl, etc.

"Heteroaryl" groups are aryl groups, as defined above, having from one to four heteroatoms in the ring structure, and may also be referred to as "aryl heterocycles" or "heteroaromatics". As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, independently selected from the group consisting of nitrogen, oxygen and sulfur. The nitrogen atom may be substituted or unsubstituted (i.e., N or NR wherein R is H or other substituents, as defined). The nitrogen and sulfur heteroatoms may optionally be oxidized (i.e., N→O and $S(O)_p$, where p=1 or 2). It is to be noted that total number of S and O atoms in the aromatic heterocycle is not more than 1.

Examples of heteroaryl groups include pyrrole, furan, thiophene, thiazole, isothiazole, imidazole, triazole, tetrazole, pyrazole, oxazole, isoxazole, pyridine, pyrazine, pyridazine, pyrimidine, and the like.

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, naphthridine, indole, benzofuran, purine, benzofuran, deazapurine, indolizine.

In the case of multicyclic aromatic rings, only one of the rings needs to be aromatic (e.g., 2,3-dihydroindole), although all of the rings may be aromatic (e.g., quinoline). The second ring can also be fused or bridged. Cycloalkyl, heterocycloalkyl, aryl, and heteroaryl can also be fused with each other. A bridged ring occurs when one or more carbon atoms link two non-adjacent carbon atoms. In one embodiment, bridge rings are one or two carbon atoms. It is noted that a bridge always converts a monocyclic ring into a tricyclic ring. When a ring is bridged, the substituents recited for the ring may also be present on the bridge. Fused (e.g., naphthyl, tetrahydronaphthyl) and Spiro rings are also included.

By "substituted" as in "substituted alkyl," and the like, it is meant that in the alkyl, or other moiety, at least one hydrogen atom bound to a carbon atom is replaced with one or more non-hydrogen substituents, e.g., by a functional group.

Examples of functional groups include, without limitation: halo, hydroxyl, sulfhydryl, $C_1$-$C_{24}$ alkoxy, $C_2$-$C_{24}$ alkynyloxy, $C_5$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO⁻), carbamoyl (—(CO)—NH$_2$), mono-substituted $C_1$-$C_{24}$ alkylcarbamoyl (—(CO)—NH($C_1$-$C_{24}$ alkyl)), di-substituted alkylcarbamoyl (—(CO)—N($C_1$-$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano (—C≡N), isocyano (—N⁺≡C⁻), cyanato (—O—C≡N), isocyanato (—O—N⁺≡C⁻), isothiocyanato (—S—C≡N), azido (—N=N⁺=N⁻), formyl (—(CO)—H), thioformyl (—(CS)—H), amino (—NH$_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_5$-$C_{20}$ arylamido (—NH—(CO)-aryl), imino (—CR=NH where R=hydrogen, $C_1$-$C_{24}$ alkyl, $C_5$-$C_{20}$ aryl, $C_6$-$C_{20}$ alkaryl, $C_6$-$C_{20}$ aralkyl, etc.), alkylimino (—CR=N(alkyl), where R=hydrogen, alkyl, aryl, alkaryl, etc.), arylimino (—CR=N(aryl), where R=hydrogen, alkyl, alkaryl, etc.), nitro (—NO$_2$), nitroso (—NO), sulfa (—SO$_2$—OH), sulfonato (—SO$_2$—O⁻), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O⁻)$_2$), phosphinato (—P(O)(O⁻)), phospho (—PO$_2$)-phosphino (—PH$_2$), mono- and di-($C_1$-$C_{24}$ alkyl)-substituted phosphino, mono- and di-($C_5$-$C_{20}$ aryl)-substituted phosphino; and the hydrocarbyl moieties such as $C_1$-$C_{24}$ alkyl (including $C_1$-$C_{18}$ alkyl, further including $C_1$-$C_{12}$ alkyl, and further including $C_1$-$C_6$ alkyl), $C_2$-$C_{24}$ alkenyl (including $C_2$-$C_{18}$ alkenyl, further including $C_2$-$C_{12}$ alkenyl, and further including $C_2$-$C_6$ alkenyl), $C_2$-$C_{24}$ alkynyl (including $C_2$-$C_{18}$ alkynyl, further including $C_2$-$C_{12}$ alkynyl, and further including $C_2$-$C_6$ alkynyl), $C_5$-$C_{30}$ aryl (including $C_5$-$C_{20}$ aryl, and further including $C_5$-$C_{12}$ aryl), and $C_6$-$C_{30}$ aralkyl (including $C_6$-$C_{20}$ aralkyl, and further including $C_6$-$C_{12}$ aralkyl). In addition, the aforementioned functional groups may, if a particular group permits, be further substituted with one or more additional functional groups or with one or more hydrocarbyl moieties such as those specifically enumerated above.

"Chiral isomer" means a compound with at least one chiral center. Compounds with more than one chiral center may exist either as an individual diastereomer or as a mixture of diastereomers, termed "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the *Sequence Rule* of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

All percentages and ratios used herein, unless otherwise indicated, are by weight.

Abbreviation Key: CMC=Critical Micelle Concentration; HLB=Hydrophilic Lipophilic Balance; IFT=Interfacial Tension; MW=Molecular Weight.

It will be appreciated that the methods disclosed herein are suitable for both large-scale and small-scale preparations of the desired compounds. In preferred embodiments of the methods described herein, the enone-glycolipid may be prepared on a large scale, for example on an industrial production scale rather than on an experimental/laboratory scale. For example, a batch-type process according to the methods of the disclosure allows the preparation of batches of at least 1 g, or at least 5 g, or at least 10 g, or at least 100 g, or at least 1 kg, or at least 100 kg of product. Furthermore, the methods allow the preparation of a product having a purity of at least 80%, at least 85%, at least 90%, at least 95%, at least 98%, or at least 98.5%. Furthermore, the methods allow the preparation of an enone glycolipid product containing no more than one impurity that is present in an amount that is greater than about 0.5%.

All patents, patent applications, and publications mentioned herein are hereby incorporated by reference in their entireties. However, where a patent, patent application, or publication containing express definitions is incorporated by reference, those express definitions should be understood to apply to the incorporated patent, patent application, or publication in which they are found, and not to the remainder of the text of this application. In the case of conflict, the present specification, including definitions, will control. The references cited herein are not admitted to be prior art to the invention.

It is to be understood that while the invention has been described in conjunction with the preferred specific embodiments thereof, that the foregoing description is intended to illustrate and not limit the scope of the invention. It will be understood by those skilled in the art that various changes may be made and equivalents may be substituted without departing from the scope of the invention, and further that other aspects, advantages and modifications will be apparent to those skilled in the art to which the invention pertains.

EXAMPLES

The following Examples are illustrative and should not be interpreted in any way so as to limit the scope of the invention.

Example 1

Representative Synthesis of Linear Enone-Linked C-Glycoside Surfactants

Synthesis of Compound 1 ((E)-1-((2S,3R,4R,5S,6R)-3,4,5-trihydroxy-6-(hydroxymethyl)tetrahydro-2H-pyran-2-yl)pentadec-3-en-2-one)

1-((2S,3R,4R,5S,6R)-3,4,5-trihydroxy-6-(hydroxymethyl)tetrahydro-2H-pyran-2-yl)propan-2-one (1.1 g, 5.0 mmol) dissolved in DMF (2 mL) was combined with 1 equivalent of pyrrolidine (410 uL, 5.0 mmol) and heptanes (4 mL). The mixture was stirred at room temperature under $N_2$ atmosphere for 10 minutes before the slow addition of 1 equivalent of dodecanal (1.2 mL, 5.0 mmol). The reaction mixture, which appeared biphasic initially, homogenized over time with stirring. Upon consumption of starting materials, the reaction mixture was cooled to room temperature and preloaded onto silica using acetone and then purified on silica gel by column chromatography using acetone for the mobile phase. Desired fractions was collected and concentrated to yield Compound 1 as a white waxy solid. δ H (500 MHz, MeOD) 6.96 (1H, dt, J 7.0, 15.9), 6.17 (1H, dd, J 7.9, 9.3), 3.76 (1H, dd, J 2.4, 11.9), 3.69 (1H, td, J 2.5, 9.2), 3.62 (1H, dd, J 5.1, 11.9), 3.34 (1H, t, J 8.7), 3.30-3.27 (1H, m), 3.23-3.18 (1H, m), 3.10 (1H, t, J 9.1), 3.01 (1H, dd, J 2.6, 16.0), 2.77 (1H, dd, J 9.0, 16.0), 2.29-2.21 (2H, m), 1.53-1.44 (2H, m), 1.37-1.25 (16H, m), 0.90 (3H, t, J 7.0); δ C (126 MHz, MeOD) 201.36, 150.61, 131.76, 81.77, 79.90, 77.49, 75.26, 71.84, 62.92, 43.73, 33.75, 33.24, 30.93, 30.91, 30.84, 30.69, 30.64, 30.51, 29.41, 23.90, 14.60; m/z (HRMS) 387.2741 (M−H+. $C_{21}H_{39}O_6$ requires 387.2741).

Other linear enone-linked C-glycoside compounds, i.e., Compounds 44-46 were synthesized via the similar method.

(E)-1-((2S,3R,4R,5S,6R)-3,4,5-trihydroxy-6-(hydroxymethyl)tetrahydro-2H-pyran-2-yl)tridec-3-en-2-one (Compound 44): δ H (400 MHz, MeOD) 6.97 (1H, dt, J 7.0, 15.9), 6.18 (1H, dt, J 1.4, 15.9), 3.77 (1H, dd, J 2.4, 11.9), 3.70 (1H, td, J 2.6, 9.2), 3.62 (1H, dd, J 5.0, 11.9), 3.38-3.33 (1H, m), 3.31-3.27 (1H, m), 3.23-3.18 (1H, m), 3.11 (1H, dd, J 8.8, 9.4), 3.02 (1H, dd, J 2.5, 16.0), 2.78 (1H, dd, J 9.0, 16.0), 2.30-2.20 (2H, m), 1.54-1.45 (2H, m), 1.38-1.26 (12H, m), 0.91 (3H, t, J 6.9); δ C (101 MHz, MeOD) 201.28, 150.57, 131.60, 81.60, 79.71, 77.31, 75.08, 71.63, 62.72, 43.54, 33.63, 33.09, 30.69, 30.57, 30.48, 30.38, 29.26, 23.77, 14.49; m/z (HRMS) 359.2435 (M+H+. $C_{19}H_{35}O_6$ requires 359.2428).

(E)-1-((2S,3R,4R,5S,6R)-3,4,5-trihydroxy-6-(hydroxymethyl)tetrahydro-2H-pyran-2-yl)undec-3-en-2-one (Compound 45): δ H (500 MHz, MeOD) 6.96 (1H, dt, J 7.0, 15.8), 6.17 (1H, d, J 15.9), 3.76 (1H, dd, J 2.3, 11.9), 3.69 (1H, td, J 2.5, 9.3), 3.62 (1H, dd, J 5.1, 11.9), 3.37-3.32 (1H, m), 3.30-3.27 (1H, m), 3.23-3.18 (1H, m), 3.11 (1H, t, J 9.1), 3.01 (1H, dd, J 2.5, 16.0), 2.77 (1H, dd, J 9.0, 16.0), 2.25 (2H, q, J 7.5), 1.54-1.46 (2H, m), 1.37-1.28 (8H, m), 0.91 (3H, t, J 6.9); δ C (126 MHz, MeOD) 201.64, 150.91, 131.98, 82.00, 80.12, 77.71, 75.48, 72.04, 63.13, 43.95, 34.00, 33.35, 30.72, 30.62, 29.65, 24.12, 14.83; m/z (HRMS) 331.2112 (M+H+. $C_{17}H_{31}O_6$ requires 331.2115).

(E)-1-((2S,3R,4R,5S,6R)-3,4,5-trihydroxy-6-(hydroxymethyl)tetrahydro-2H-pyran-2-yl)non-3-en-2-one (Compound 46): b H (500 MHz, MeOD) 6.96 (1H, dt, J 7.0, 15.8), 6.18 (1H, d, J 15.9), 3.76 (1H, dd, J 2.1, 11.8), 3.69 (1H, td, J 2.5, 9.7), 3.62 (1H, dd, J 5.1, 11.9), 3.37-3.32 (1H, m, J 8.8), 3.30-3.26 (1H, m), 3.23-3.17 (1H, m), 3.10 (1H, t, J 9.1), 3.00 (1H, dd, J 2.3, 15.9), 2.77 (1H, dd, J 9.0, 16.0), 2.31-2.20 (2H, m, J 1.3, 8.0), 1.56-1.46 (2H, m), 1.43-1.22 (4H, m), 0.92 (3H, t, J 6.5); δ C (126 MHz, MeOD) 201.59, 150.86, 131.99, 82.01, 80.12, 77.71, 75.48, 72.05, 63.13, 43.94, 33.96, 32.97, 29.33, 23.92, 14.73; m/z (HRMS) 325.1626 (M+Na+. $C_{15}H_{26}NaO_6$ requires 325.1626).

It was observed that reaction in a biphasic system of NN-dimethylformamide (DMF) and heptane in the presence of 1.0 equivalent of aldehyde, the yield of linear enones was greatly enhanced. It was also observed that the purified products also contained a trace of the enone's deconjugated analog, represented as Compounds 47 and 48. As suggested by Jorgensen et al., *Tet. Lett.* 1964, 19, 1203, the equilibrium of this isomerization event can be shifted dramatically in favor of the deconjugated product through use of UV irradiation. Accordingly, when Compound 1 was irradiated with UV lamps for 6 hrs in MeOH the result was >80% conversion to an unassigned mixture of Compounds 47 and 48 (~2.25:1) as determined by quantitative $^{13}C$ NMR spectroscopy. δ H (500 MHz, MeOD) 5.59-5.44 (2H, m), 3.74 (1H, dd, J 2.3, 11.9), 3.64-3.58 (2H, m), 3.30-3.23 (3H, m), 3.21-3.17 (2H, m), 3.04 (1H, t, J 9.2), 2.85 (1H, dd, J 2.9, 16.0), 2.63-2.53 (1 H, m), 2.05-196 (2H, m), 1.36-1.31 (2H, m), 1.26-1.25 (14H, m), 0.86 (3H, t, J 6.6); $δ_C$ (126 MHz, MeOH) 210.03, 135.74, 123.01, 81.27, 79.31, 76.84, 74.78, 71.37, 62.58, 47.83, 45.70, 32.86, 30.55, 30.48, 30.42, 30.32, 30.26, 30.17, 30.08, 23.55, 14.39 m/z (HRMS) 387.2741 (M+H+. $C_{21}H_{39}O_6$ requires 387.2741).

Example 2

Representative Synthesis of Cyclic Enone-Linked C-Glycoside Surfactants

Synthesis of Compound 2 (4-ethyl-5-propyl-2-((2S, 3R,4R,5S,6R)-3,4,5-trihydroxy-6-(hydroxymethyl)tetrahydro-2H-pyran-2-yl)cyclohex-2-enone)

In a round bottom flask, nonulose (400 mg, 1.8 mmol) was dissolved in MeOH (2.0 ml) and stirred with a stir bar at room temperature under $N_2$ atmosphere. Pyrrolidine (150 ul, 1.8 mmol) was then introduced, followed by butyraldehyde (342 ul, 3.8 mmol), and the solution was stirred vigorously for 48 hours. The solution was then extracted 2× with heptane, diluted with n-butanol, and washed 2× with $H_2O$. Centrifugation was used to break emulsions as needed. The organic phase was then treated with Amberlite IR-120 H$^+$ ion exchange resin until the pale yellow solution became completely colorless. The solution was then filtered and concentrated to give Compound 2: δ H (500 MHz, MeOH) 7.04 (1H, s), 4.17 (1H, d, J 9.9), 3.82 (1H, d, J 11.9), 3.70-3.60 (1H, m), 3.44-3.32 (3H, m), 3.30-3.25 (1H, m), 2.59 (1H, dd, J 15.9, 28.8), 2.32-2.14 (2H, m), 2.03-1.87 (1H, m), 1.81-1.69 (1H, m), 1.68-1.49 (2H, m), 1.48-1.36 (1H, m), 1.35-1.24 (2H, m), 1.00 (3H, t, J 7.4), 0.93 (3H, t, J 6.3); δ C (126 MHz, MeOH) 201.04, 154.92, 138.29, 82.72, 80.40, 76.56, 76.26, 72.21, 63.37, 44.29, 43.38, 38.81, 36.67, 25.96, 21.00, 14.90, 11.66; m/z (HRMS) 329.1955 (M+H$^+$. $C_{17}H_{29}O_6$ requires 329.1959).

Synthesis of Compound 3 (4-butyl-5-pentyl-2-((2S, 3R,4R,5S,6R)-3,4,5-trihydroxy-6-(hydroxymethyl) tetrahydro-2H-pyran-2-yl)cyclohex-2-enone)

Following the similar procedure described above, nonulose (6.5 g, 29.5 mmol) in MeOH (20 ml) was combined with pyrrolidine (2.4 ml, 29.5 mmol), and hexanal (7.6 ml, 62.0 mmol). Upon workup, Compound 3 was obtained as an off-white solid: δ H (500 MHz, MeOH) 7.03 (1H, d, J 2.9), 4.17 (1H, d, J 9.6), 3.82 (1H, d, J 11.9), 3.68-3.62 (1H, m), 3.44-3.32 (3H, m), 3.30-3.25 (1H, m), 2.62 (1H, dd, J 4.0, 16.0), 2.39-2.27 (1H, m), 2.19 (1H, dd, J 9.7, 16.0), 1.99-1.85 (1H, m), 1.74-1.61 (1H, m), 1.61-1.49 (2H, m), 1.41-1.24 (11H, m), 0.95 (3H, t, J 5.5), 0.91 (3H, t, J 6.8); δ C (126 MHz, MeOD) 200.57, 154.55, 137.56, 82.27, 79.97, 76.14, 75.89, 71.78, 62.93, 42.91, 42.47, 39.60, 39.15, 33.94, 33.03, 32.60, 29.97, 27.18, 23.99, 23.62, 14.34; m/z (HRMS) 385.2587 (M+H$^+$. $C_{21}H_{37}O_6$ requires 385.2585).

Synthesis of Compounds 28-31 (4-ethyl-5-heptyl-2-((2S,3R,4R,5S,6R)-3,4,5-trihydroxy-6-(hydroxymethyl)tetrahydro-2H-pyran-2-yl)cyclohex-2-enone)

To a solution of Compound 45 (100 mg, 0.3 mmol) in MeOH (0.5 ml) was added pyrrolidine (25 ul, 0.3 mmol), followed by butyraldehyde (29 ul, 0.32 mmol). The reaction mixture was then stirred for 36 hours and was worked up by extracting 2× with heptane, concentrating the MeOH phase, and dissolving the resulting residue in 2 ml of n-butanol. The butanol phase was then washed 2× with $H_2O$ and then stirred with Amberlite IR-120 H$^+$ ion exchange resin until the pale yellow solution became colorless. The solution was then filtered and concentrated to give a mixture of Compounds 28-31 as a colorless solid residue: δ H (500 MHz, MeOD) 7.04 (1H, d, J 3.2), 4.17 (1H, d, J 9.4), 3.82 (1H, dd, J 2.1, 11.9), 3.68-3.62 (1H, m), 3.42-3.32 (3H, m), 3.29-3.25 (1H, m), 2.62 (1H, dd, J 4.3, 16.1), 2.32-2.15 (2H, m), 1.99-1.88 (1H, m), 180-1.69 (1H, m), 1.68-1.52 (2H, m), 1.44-1.37 (1H, m), 1.35-1.28 (10H, m), 1.00 (3H, t, J 7.4), 0.90 (3H, t, J 6.9); δ$_C$ (126 MHz, MeOD) 200.64, 154.47, 137.84, 82.27, 79.98, 76.13, 75.82, 71.79, 62.95, 43.88, 42.99, 38.61, 33.92, 32.98, 30.76, 30.34, 27.46, 25.53, 23.67, 14.38, 11.22; m/z (HRMS) 385.2585 (M+H$^+$. $C_{21}H_{37}O_6$ requires 385.2585).

Example 3

Critical Micelle Concentration (CMC)

The CMC for compounds of the invention is determined using known methods in the art. FIG. 1 shows a comparison of CMC curves for selected surfactants between series.

As can be seen from the CMC trends when looking at surfactants with similar Hydrophilic Lipophilic Balances (HLBs) and Molecular Weights (MWs) between series, there are significantly different surface activities that result from the structural composition of the surfactants. From this data, it can also be seen that the Compound 3 has both the greatest reduction in Interfacial Tension (IFT) and very low estimated CMC, a very desirable combination of properties.

As also can be seen in Table 1 below, the C-glycosides behave very similarly to their O-glycoside counterparts in terms of CMC and IFT (γ) reduction (the surface tension measurements were obtained using a Sigma 7$^{03}$ Tensiometer equipped with a Typ T107B Pt plate; all experiments were conducted at room temperature using DI water, which was calibrated to 72.7±0.2 mN/m). Further, it appears that the CMC is directly related to the hydrophobic-lipophilic balance (HLB), as calculated according to Griffin's Method. Indeed the CMC region increasingly broadened as the HLB increased, which is a common phenomenon often attributed to polydispersity of micelles. See, e.g., Pasquali, R. C.; Taurozzi, M. P.; Bregni, C. *Int. J. Pharm.* 2008, 356, 44; and Mukerjee, P.; Mysels, K. J. *Critical Micelle Concentrations of Aqueous Surfactant Systems*. U.S. Department of Commerce, 1970, p. 14.

TABLE 1

| Compound | CMC (mM) | γ$_{min}$ (mN/m) | HLB$^a$ |
|---|---|---|---|
| 46 | 3.9 | 24 | 13.6 |
| 1 | 0.1 | 28 | 10.6 |
| 2 | 52.2 | 30 | 12.5 |
| 3 | 0.17 | 22 | 10.6 |
| Octyl-AG$^b$ | 18.0 | 24 | 12.3 |
| Dodecyl-AG$^b$ | 0.17 | 24 | 10.3 |

$^a$HLB = Hydrophobic Lipophilic Balance according to Griffin's Method
$^b$AG = O-AlkylGlucoside (see Rybinski, W. v.; Hill, K. *Angew. Chem. Int. Ed.* 1998, 37, 1328.)

Figure 2:
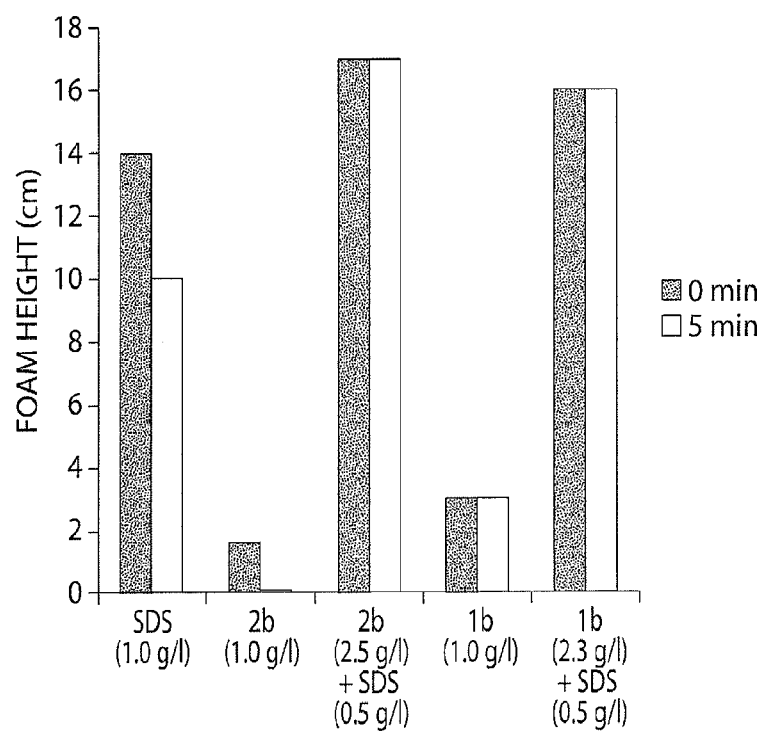
FIG. 2 is a graph that shows Ross-Miles foam test results for solutions of SDS and and selected C-glycoside surfactants.

Finally, foaming properties were evaluated using the Ross-Miles foam test according to the known ASTM protocol (i.e., ASTM Standard D1173, 2007, ASTM International, DOI: 10.15201D1173-07.) As shown in FIG. 2, compared to SDS, the foaming properties of the C-glycosides were modest, with Compound 3 (denoted as "2b") exhibiting virtually no excess foam after 5 minutes. However, unexpectedly, when Compound 3 was combined with SDS as a 20% solution, the foaming properties exceeded that of SDS alone and the foam height remained unchanged over 5 minutes. Compound 1 (denoted as "1d") also exhibited similar unexpected behavior, suggesting that the C-glycosides have a foam enhancing and stabilizing effect in the presence of an anionic surfactant.

It was also observed that Compounds 47 and 48, the photoisomers of Compound 1, unexpected exhibited substanitally the same behavior in terms of CMC, interfacial tension (γ) reduction, as well as the foam enhancing and stablizing capability.

Example 4

Representative Synthesis of cyclic Enone-Linked C-Glycoside Surfactants with Modified Sugar Moiety Synthesis of Compound 32

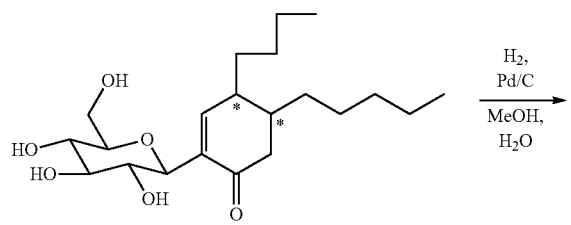

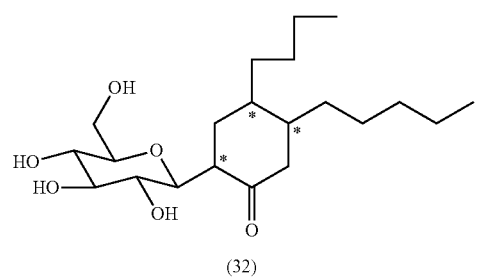

(32)

4-Butyl-5-pentyl-2-((2S,3R,4R,5S,6R)-3,4,5-trihydroxy-6-(hydroxymethyl)tetrahydro-2H-pyran-2-yl)cyclohex-2-enone (8.3 g, 21.6 mmol) was dissolved in methanol (MeOH) and was charged with ~800 mgs of Pd/C (20%, wet). The mixture was placed under 800 psi $H_2$ atmosphere with mechanical stirring in a Parr reactor. After 24 hrs, the solution was removed from the reactor and rinsed through celite with MeOH and $H_2O$. The mixture was then concentrated to give a light yellow residue (8.2 g). $^1H$ NMR showed the full disappearance of characteristic enone protons (~7.0-7.2 ppm) and all required protons for desired product. m/z (HRMS) 387.27403 (expected [M+H$^+$]=387.274115 for 2S,3R,4R,5S,6R)-2-(3-butyl-6-hydroxy-4-pentylcyclohex-1-enyl)-6-(hydroxymethyl)tetrahydro-2H-pyran-3,4,5-triol, $C_{21}H_{38}O_6$).

Synthesis of Compound 33

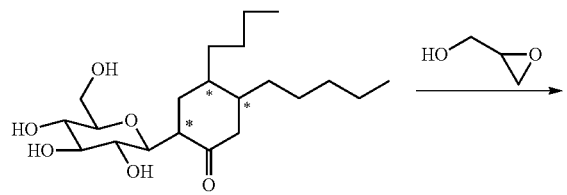

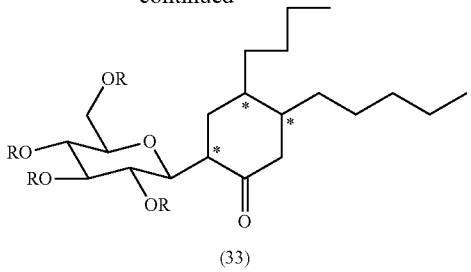

(33)

$$R = \left\{ \begin{array}{c} OH \\ \diagup \diagdown \diagup \diagdown \\ O \end{array} \right\}_n H$$

4-Butyl-5-pentyl-2-((2S,3R,4R,5S,6R)-3,4,5-trihydroxy-6-(hydroxymethyl)tetrahydro-2H-pyran-2-yl)cyclohexanone (16.0 g) was combined with glycidol (16 ml) in a round bottomed flask and placed on a rotary eveporator. The mixture was spun in a water bath at 85° C. for 1 hour under light vaccuum pressure. After one hour, the solution was cooled to room temperature, dissolved in n-butanol, and washed 3× with $H_2O$. The n-butanol phase was then concentrated. 23.2 g was recovered after thorough drying. Added mass corresponds to ~2-2.5 equivalents of glycidol incorporation. $^1H$ NMR showed a ratio ~1.1:1.4 of protons in the 3.0-4.0 ppm region relative to the 0.8-1.8 ppm region. m/z (HRMS) 483.29297 (expected [M+Na$^+$]=483.292840 where n=1), Synthesis of Compound 34

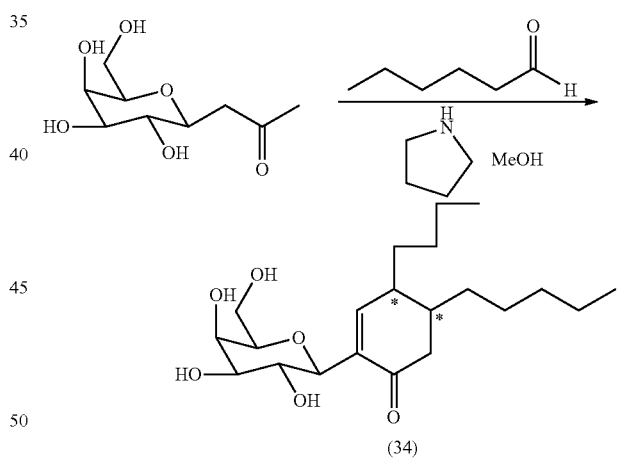

(34)

1.24 g of 1-((2S,3R,4R,5R,6R)-3,4,5-trihydroxy-6-(hydroxymethyl)tetrahydro-2H-pyran-2-yl)propan-2-one (*Aust. J. Chem.* 2002, 55, 147-154; *Bioorg. Med. Chem. Lett.* 2009, 19, 845-849) was combined with MeOH (10 ml), pyrrolidine (0.464 ml), and hexanal (1.5 ml). The solution was then stirred for 48 hrs at room temperature, was extracted 3× with heptane, and the methanolic phase was then concentrated. The residue was then dissolved in n-butanol and washed 3× with $H_2O$. The n-butanol phase was then stirred in the presence of Dowex H$^+$ resin for 30 minutes before filtering and concentrating. The resulting residue (1.5 g) showed all required protons by $^1H$ NMR including characteristic enone protons in the 7.0-7.3 ppm range. HRMS showed [M+Na$^+$]= 407.24083 (expected [M+Na$^+$]=407.2404 for 4-butyl-5- pentyl-2-((2S,3R,4R,5R,6R)-3,4,5-trihydroxy-6-(hydroxymethyl)tetrahydro-2H-pyran-2-yl)cyclohex-2-enone, $C_{21}H_{36}O_6$).

Synthesis of Compound 35

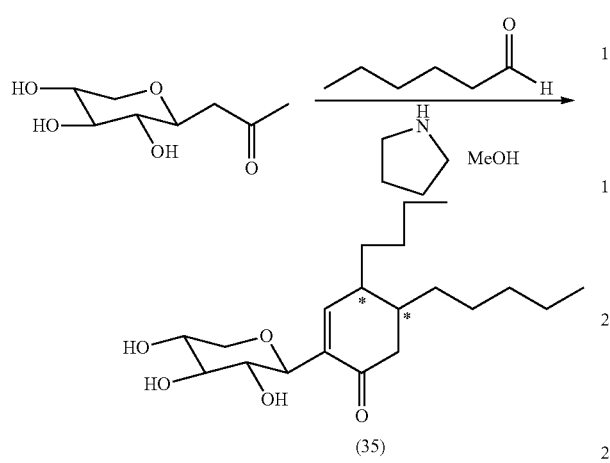

(35)

1.25 g of 1-((2S,3R,4S,5R)-3,4,5-trihydroxytetrahydro-2H-pyran-2-yl)propan-2-one (*Aust. J. Chem.* 2002, 55, 147-154; *Bioorg. Med. Chem. Lett.* 2009, 19, 845-849) was combined with MeOH (10 ml), pyrrolidine (0.55 ml), and hexanal (1.8 ml). The solution was then stirred for 48 hrs at room temperature, extracted 3× with heptane, and the methanolic phase was then concentrated. The residue was dissolved in n-butanol and washed 3× with $H_2O$. The n-butanol phase was then stirred in the presence of Dowex $H^+$ resin for 30 minutes before filtering and concentrating. The resulting residue (1.2 g) showed all required protons including characteristic enone protons in the 6.8-7.2 ppm range. Routine MS showed $[M+H^+]=355.26$. (expected $[M+H^+]=355.25$ for 4-butyl-5-pentyl-2-((2S,3R,5R)-3,4,5-trihydroxytetrahydro-2H-pyran-2-yl)cyclohex-2-enone, $C_{20}H_{34}O_5$). HRMS showed [M+Na+]=377.22963 (expected mass for [M+Na+] =377.229846).

Synthesis of Compound 36

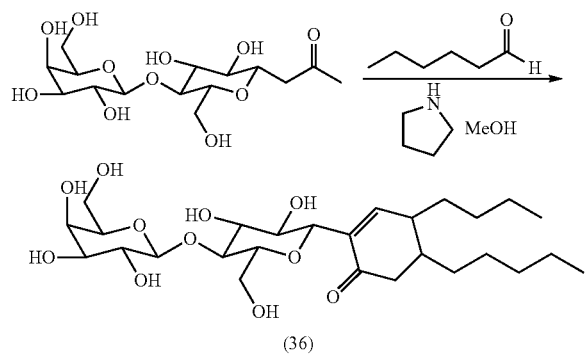

(36)

934 mg of 1-((2S,3R,4S,5S,6R)-3,4-dihydroxy-6-(hydroxymethyl)-5-((2S,3R,4S,5R,6R)-3,4,5-trihydroxy-6-(hydroxymethyl)tetrahydro-2H-pyran-2-yloxy)tetrahydro-2H-pyran-2-yl)propan-2-one (*Bioorg. Med. Chem. Lett.* 2009, 19, 845-849) was combined with MeOH (10 ml), pyrrolidine (0.2 ml), and hexanal (0.66 ml). The solution was then stirred for 48 hrs at room temperature, was extracted 3× with heptane, and the methanolic phase was then concentrated. The residue was dissolved in n-butanol and washed 3× with $H_2O$. The n-butanol phase was then stirred in the presence of Dowex $H^+$ resin for 30 minutes before filtering and concentrating. The resulting residue (648 mg) showed all required protons including characteristic enone protons in the 7.0-7.3 ppm range. HRMS showed $[M+H^+]=547.31200$ (expected mass $[M+H^+]=547.311289$ for 4-butyl-2-((2S,3R,4S,5S,6R)-3,4-dihydroxy-6-(hydroxymethyl)-5-((2S,3R,4S,5R,6R)-3,4,5-trihydroxy-6-(hydroxymethyl)tetrahydro-2H-pyran-2-yloxy)tetrahydro-2H-pyran-2-yl)-5-pentylcyclohex-2-enone, $C_{27}H_{46}O_{11}$).

Synthesis of Compound 37

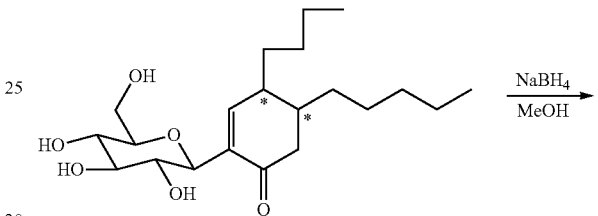

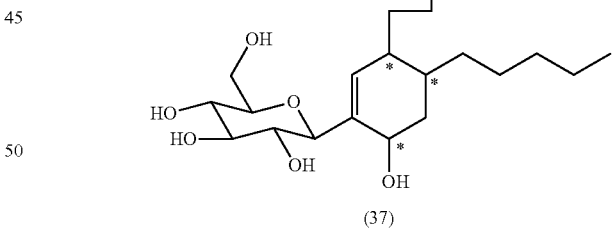

(37)

380 mg of 4-butyl-5-pentyl-2-((2S,3R,4R,5S,6R)-3,4,5-trihydroxy-6-(hydroxymethyl)tetrahydro-2H-pyran-2-yl)cyclohex-2-enone was dissolved in 5 ml MeOH and charged with 19 mg of $NaBH_4$ (slight fizzing). The solution was then stirred for 1 hour, diluted with 5 ml 1N HCl (aq) and stirred for 20 minutes. The solution was then diluted with n-butanol and $H_2O$ and partitioned. The n-butanol phase was then washed 2× with $H_2O$ and concentrated. 324 mg of residue was recovered. $^1H$ NMR showed expected shift in olefinic protons to the 5.6-6.0 ppm region with all other required protons present. HRMS showed $[M+Na^+]=409.25623$ (expected mass=409.256060 for (2S,3R,4R,5S,6R)-2-(3-butyl-6-hydroxy-4-pentylcyclohex-1-enyl)-6-(hydroxymethyl)tetrahydro-2H-pyran-3,4,5-triol, $C_{21}H_{38}O_6$).

Synthesis of Compound 38

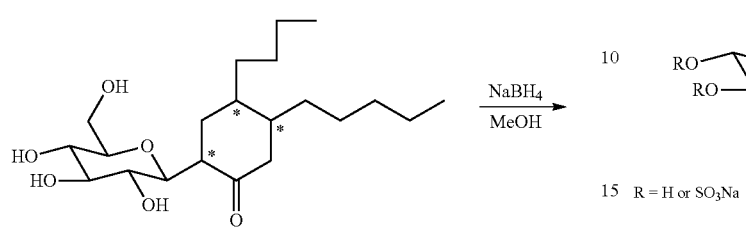

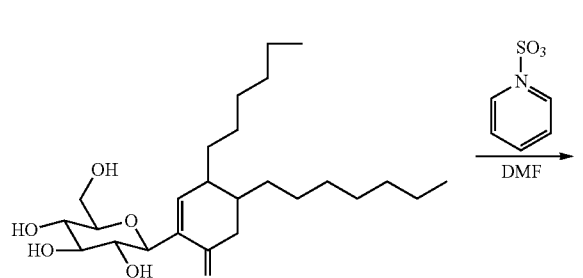

70 mg of 4-butyl-5-pentyl-2-((2S,3R,4R,5S,6R)-3,4,5-trihydroxy-6-(hydroxymethyl)tetrahydro-2H-pyran-2-yl)cyclohexanone was dissolved in 5 ml MeOH and charged with 19 mg of $NaBH_4$ (slight fizzing). The solution was then stirred for 1 hour, diluted with 5 ml 1 N HCl (aq) and stirred for 20 minutes. The solution was then diluted with n-butanol and $H_2O$ and partitioned. The n-butanol phase was then washed 2× with $H_2O$ and concentrated. 67 mg of residue was recovered. $^1$H NMR showed disappearance of protons in the 2.0-2.5 ppm region and all other required protons present. HRMS showed [M+Na$^+$]=411.27193 (expected mass=411.271710 for (2S,3R,4R,5S,6R)-2-(5-butyl-2-hydroxy-4-pentylcyclohexyl)-6-(hydroxymethyl)tetrahydro-2H-pyran-3,4,5-triol, $C_{21}H_{40}O_6$).

Synthesis of Compound 39

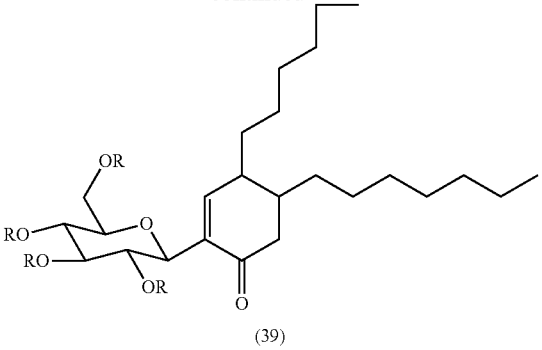

R = H or $SO_3Na$ 5-heptyl-4-hexyl-2-((2S,3R,4R,5S,6R)-3,4,5-trihydroxy-6-(hydroxymethyl)tetrahydro-2H-pyran-2-yl)cyclohex-2-enone (730 mg, 1.66 mmol) was dissolved in 10 ml N,N-dimethylformamide (DMF) and was charged with 470 mg of pyridinium stabilized sulfur trioxide (50-60% active). The mixture was then heated at 50° C. for 18 hours. The solution was allowed to cool to room temperature and was diluted with $H_2O$ and n-butanol. The organic and aqueous layers were partitioned and the aqueous layer was treated with sodium bicarbonate until fizzing subsided. The aqueous layer was then concentrated and the solid residue was extracted with methanol and concentrated. 410 mg of light yellow foam resulted. $^1$H NMR showed peaks consistent with sulfonated starting material, with characteristic proton shifts in the 4.0-4.2 ppm range. HRMS shows [M+Na+]=565.24150 (expected mass for [M+Na+]=565.259825).

Synthesis of Compound 40

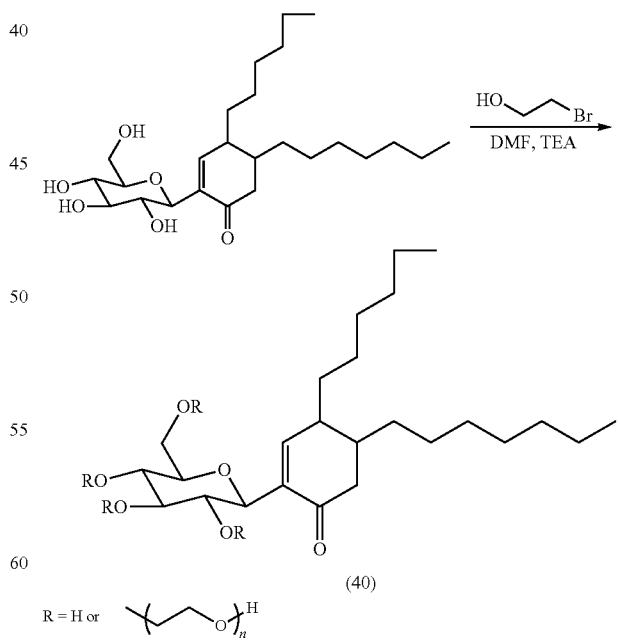

5-heptyl-4-hexyl-2-((2S,3R,4R,5S,6R)-3,4,5-trihydroxy-6-(hydroxymethyl)tetrahydro-2H-pyran-2-yl)cyclohex-2-enone (1.25 g, 2.84 mmol) was dissolved in 10 ml N,N- dimethylformamide (DMF) and was charged with 1.4 ml of triethylamine and 0.605 ml of 2-bromoethanol. The mixture was then heated at 50° C. for 18 hours. After 18 hours, the solution was allowed to cool to room temperature and was diluted with H$_2$O and n-butanol. The organic and layer was washed with H$_2$O three times and was then concentrated. 1.13 g of light brown residue resulted. $^1$H NMR showed peaks consistent with ethoxylated starting material, with characteristic proton shifts in the 3.4-3.8 ppm range.

What is claimed is:

1. A compound of formula B:

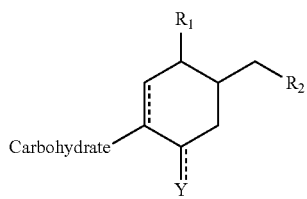

(B)

wherein Carbohydrate is a C-linked glycoside, each of $R_1$ and $R_2$ independently, is hydrogen, linear alkyl, branched alkyl, substituted linear alkyl, substituted branched alkyl, cycloalkyl, or substituted cycloalkyl, each of the two dotted lines ------, independently, is absent or a bond, and Y is O or OR$_8$, in which R$_8$ is hydrogen or $C_1$-$C_{10}$ alkyl.

2. The compound of claim 1, wherein each of $R_1$ and $R_2$, independently, is saturated or unsaturated alkyl.

3. The compound of claim 2, wherein the alkyl has one degree of unsaturation.

4. The compound of claim 1, wherein each of $R_1$ and $R_2$ independently, is alkyl having 2, 3, 4, 5, 6, 7, 8, 9, 10, 11, or 12 carbon atoms.

5. The compound of claim 1, wherein each of $R_1$ and $R_2$ independently, is alkyl having 13, 14, 15, 16, 17, 18, 19, 20, 21, or 22 carbon atoms.

6. The compound of claim 1, wherein Carbohydrate is a mono- or polysaccharide or a glycosidic derivative thereof.

7. The compound of claim 1, wherein Carbohydrate is glucose, xylose, lyxose, mannose, maltose, cellobiose, galactose, or a glycosidic derivative thereof.

8. The compound of claim 4, wherein each of $R_1$ and $R_2$, independently, is saturated alkyl.

9. The compound of claim 8, wherein Carbohydrate is a mono- or polysaccharide or a glycosidic derivative thereof.

10. The compound of claim 8, wherein Carbohydrate is glucose, xylose, lyxose, mannose, maltose, cellobiose, galactose, or a glycosidic derivative thereof.

11. The compound of claim 8, wherein the both of the two dotted lines ------ are each a bond.

12. The compound of claim 8, wherein one of the two dotted lines ------ is absent and the other is a bond.

13. The compound of claim 12, wherein Y is O.

14. The compound of claim 1, wherein the compound is of formula Ib:

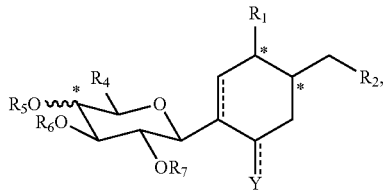

(Ib)

wherein each of $R_1$ and $R_2$ independently is H, or $C_1$-$C_{24}$ alkyl optionally substituted with COOR$_a$, R$_a$ being H, $C_1$-$C_{10}$ alkyl, $C_3$-$C_8$ cycloalkyl, aryl, or heteroaryl;

$R_4$ is CH$_2$OR$_b$ or COOR$_b$, in which R$_b$ is H, sulfo, sulfonato, phosphono, phosphonato, COR$_c$, R$_c$ being hydroxy, $C_1$-$C_{10}$ alkoxy, or $C_1$-$C_{10}$ alkyl optionally substituted with one or more groups selected from carboxy, carboxylato, sulfo, sulfonato, phosphono, and phosphonato, or R$_b$ is $C_1$-$C_{10}$ alkyl optionally substituted with one or more groups selected from carboxy, carboxylato, sulfo, sulfonato, phosphono, phosphonato, —(CH$_2$CH$_2$O)$_n$H, and —(CH$_2$CHOHCH$_2$O)$_n$H, n being 1, 2, 3, 4, 5, 6, 7, 8, 9, or 10; and each of $R_5$, $R_6$, and $R_7$, independently, is H, sulfo, sulfonato, phosphono, phosphonato, COR$_c$, a monosaccharide or a glycosidic derivative thereof, or $C_1$-$C_{10}$ alkyl optionally substituted with one or more groups selected from carboxy, carboxylato, sulfo, sulfonato, phosphono, phosphonato, —(CH$_2$CH$_2$O)$_n$H, and —(CH$_2$CHOHCH$_2$O)$_n$H.

15. The compound of claim 14, wherein each of $R_1$ and $R_2$ independently is $C_2$-$C_5$ alkyl optionally substituted with COOR$_a$.

16. The compound of claim 14, wherein each of $R_1$ and $R_2$ independently is $C_6$-$C_{22}$ alkyl optionally substituted with COOR$_a$.

17. The compound of claim 14, wherein at least one of $R_5$, $R_6$, and $R_7$ is sulfo, sulfonato, phosphono, phosphonato, COR$_c$, a monosaccharide or a glycosidic derivative thereof, or $C_1$-$C_{10}$ alkyl optionally substituted with one or more groups selected from carboxy, carboxylato, sulfo, sulfonato, phosphono, phosphonato, —(CH$_2$CH$_2$O)$_n$H, and —(CH$_2$CHOHCH$_2$O)$_n$H and the others are each hydrogen.

18. The compound of claim 17, wherein $R_5$ is a monosaccharide or a glycosidic derivative thereof.

19. The compound of claim 18, wherein $R_5$ is glucose, xylose, lyxose, mannose, galactose, or a glycosidic derivative thereof.

20. The compound of claim 14, wherein $R_4$ is CH$_2$OR$_b$ and at least one of R$_b$, $R_5$, $R_6$, and $R_7$ is sulfo, sulfonato, phosphono, phosphonato, COR$_c$, or $C_1$-$C_{10}$ alkyl optionally substituted with one or more groups selected from carboxy, carboxylato, sulfo, sulfonato, phosphono, phosphonato, —(CH$_2$CH$_2$O)$_n$H, and —(CH$_2$CHOHCH$_2$O)$_n$H and the others are each hydrogen.

21. The compound of claim 14, wherein R$_b$, $R_5$, $R_6$, and $R_7$ are each hydrogen.

22. The compound of claim 14, wherein the both of the two dotted lines ------ are absent or each a bond.

23. The compound of claim 14, wherein one of the two dotted lines ------ is absent and the other is a bond.

24. The compound of claim 14, wherein Y is O.

25. The compound of claim 14, wherein Y is OH.

26. The compound of claim 14, wherein the compound is (2)
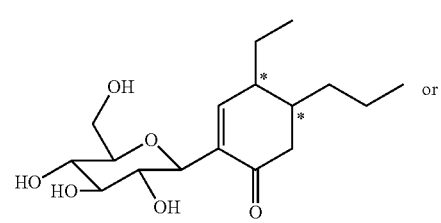 or
(3)
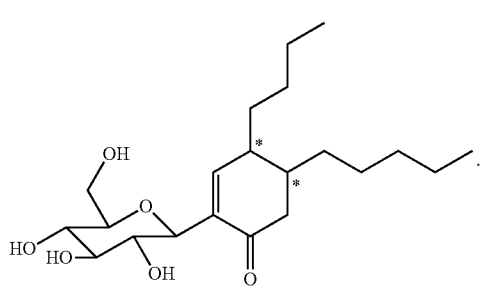
27. The compound of claim 1, wherein the compound is any of the following compounds:
(4)
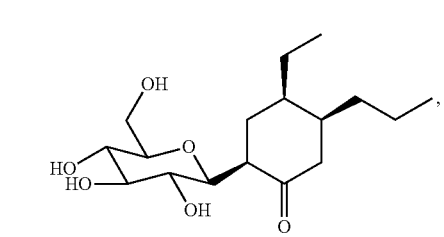
(5)
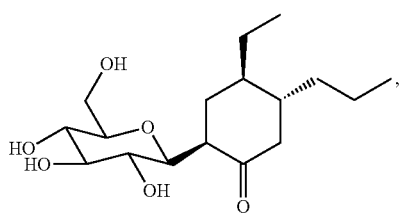
(6)
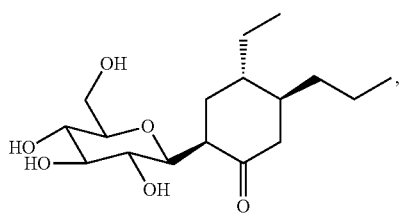
(7)
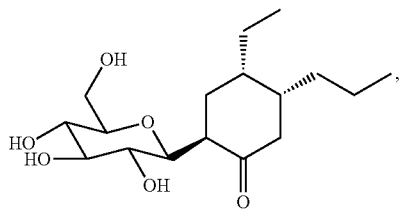
(8)
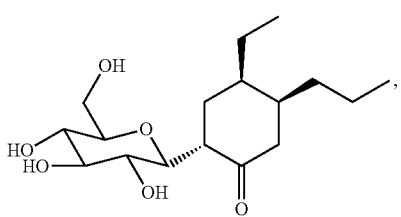
(9)
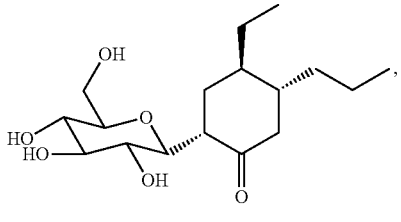
(10)
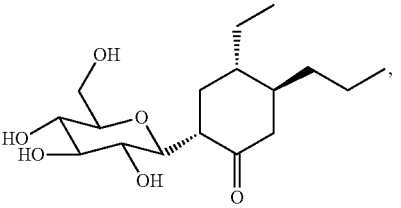
(11)
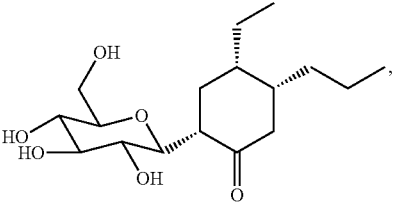
(12)
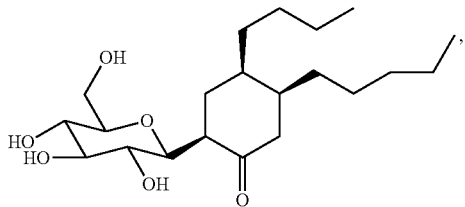
(13)
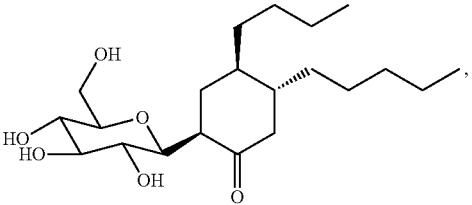
(14)
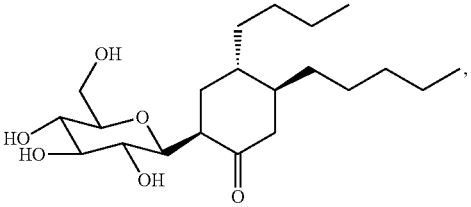

-continued
(15)
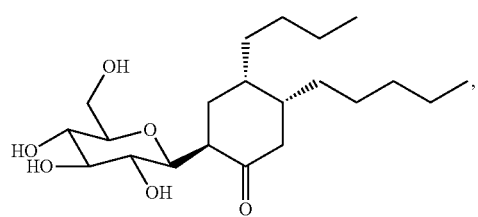
(16)
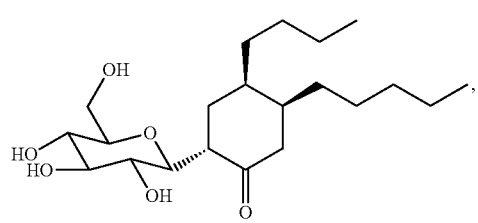
(17)
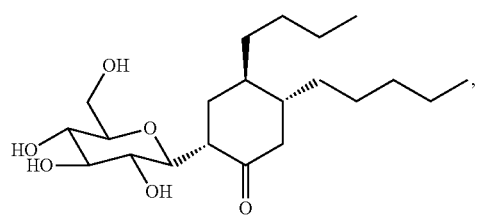
(18)
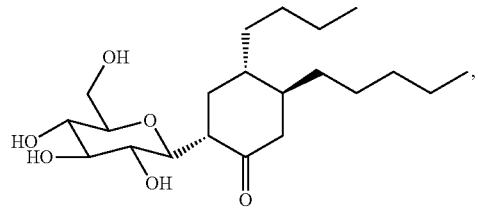
(19)
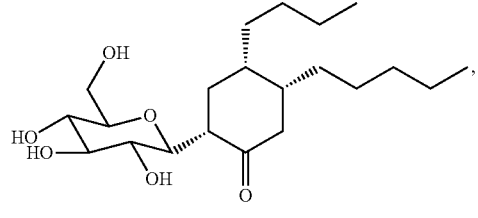
(20)
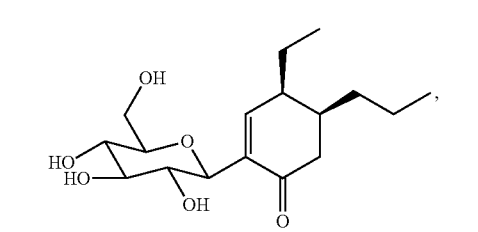
(21)
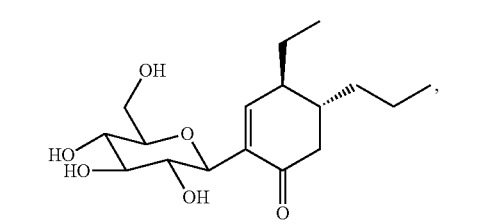
-continued
(22)
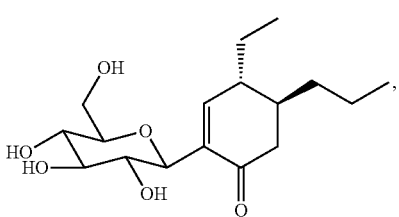
(23)
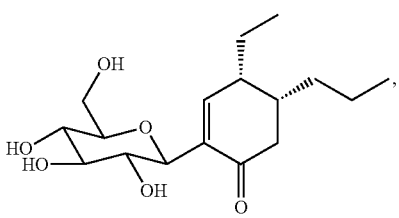
(24)
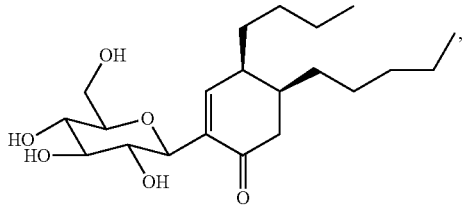
(25)
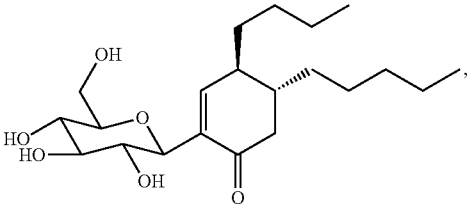
(26)
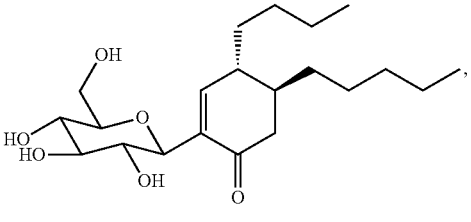
(27)
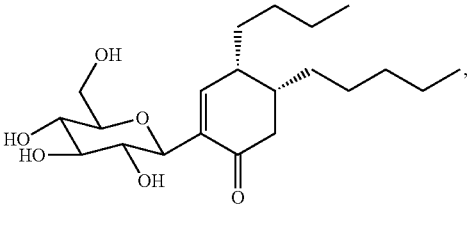
(28)
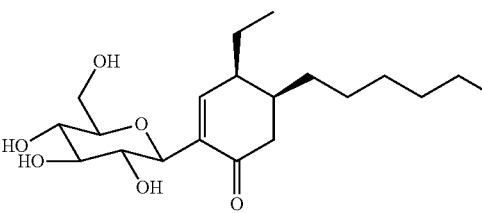

53
-continued
(29)
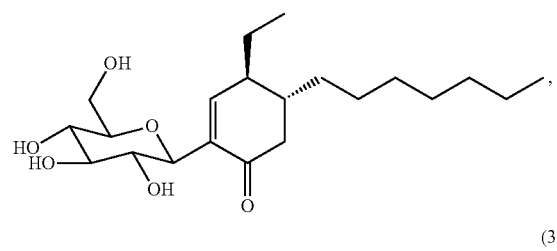
(30)
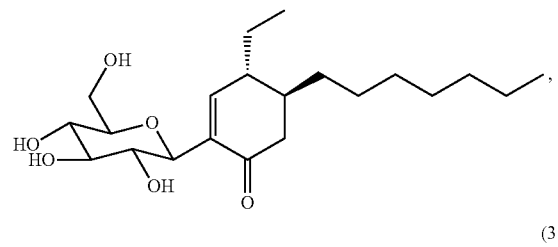
(31)
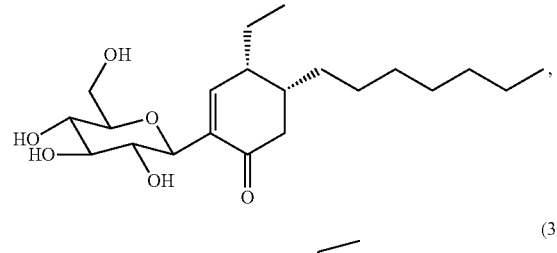
(32)
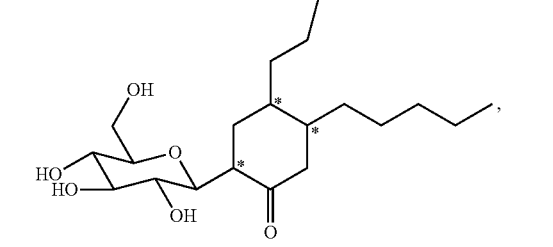
(33)
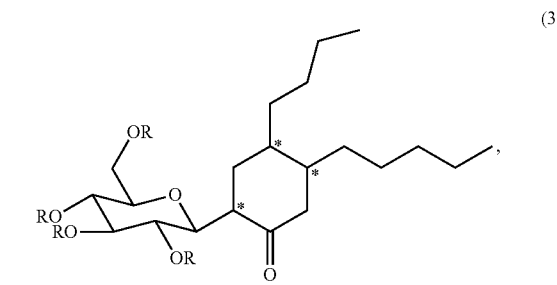
(34)
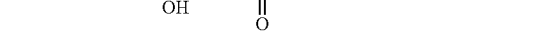
54
-continued
(35)
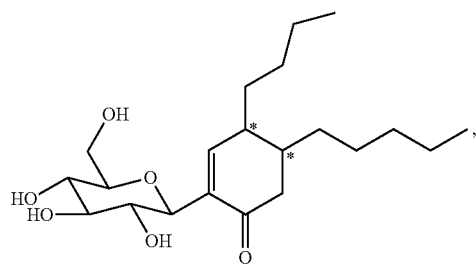
(36)
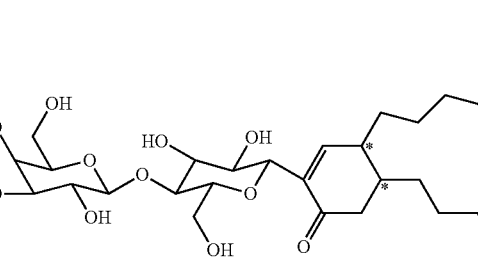
(37)
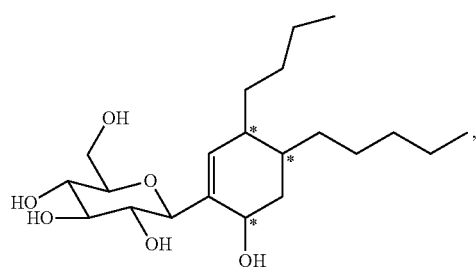
(38)
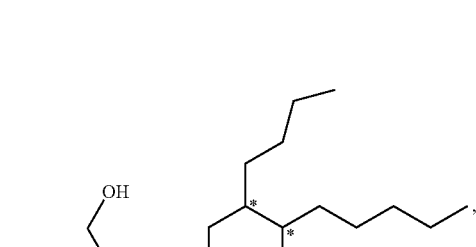
(39)
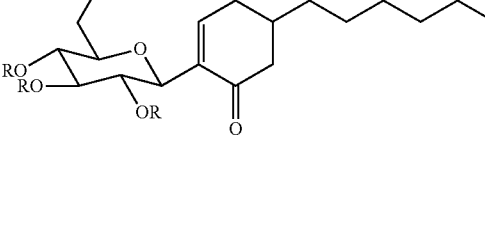

in which each R independently is H or SO₃Na, (40)

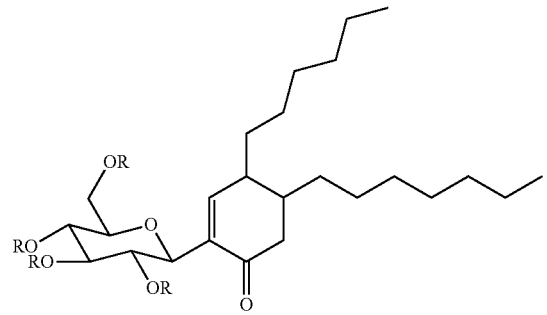

in which each R independently is H or —(CH₂CH₂O)ₙ—H with n being 1, 2, or 3, (41)

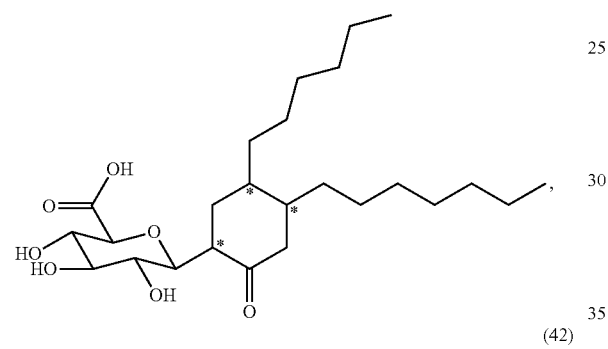

, (42)

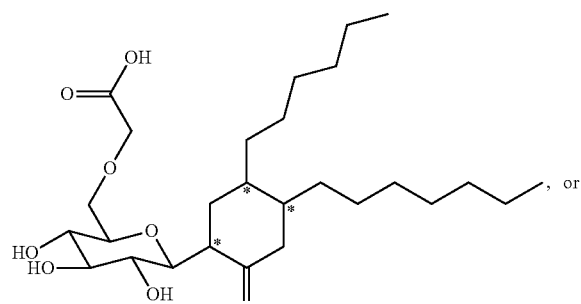

, or (43)

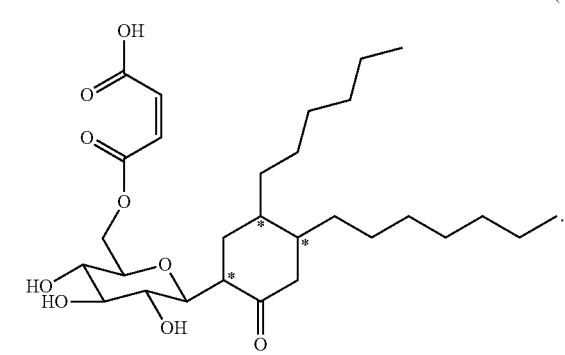

.

28. A composition comprising a compound according to any one of claim 27.

29. The composition of claim 28, further comprising a surfactant.

30. The composition of claim 29, wherein the surfactant is anionic.

31. A method of synthesizing a compound of formula B

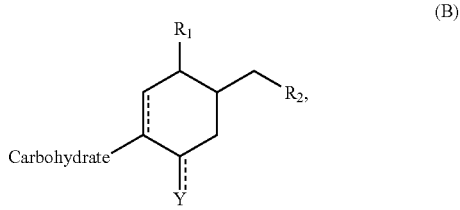

(B)

wherein Carbohydrate is a C-linked glycoside, each of $R_1$ and $R_2$ independently, is hydrogen, linear alkyl, branched alkyl, substituted linear alkyl, substituted branched alkyl, cycloalkyl, or substituted cycloalkyl, each of the two dotted lines ------, independently, is absent or a bond, and Y is O, the method comprising:

reacting a Carbohydrate-containing ketone with excess alkyl aldehyde in an alkaline solution to form a compound of formula B in which each of the dotted lines is a bond and Y is O, and optionally further comprising reducing the compound of formula B in which each of the dotted lines is a bond and Y is O to form a compound of formula B in which at least one of the dotted lines is absent.

32. The method of claim 31, wherein the Carbohydrate is a mono- or polysaccharide or a glycosidic derivative thereof.

33. The method of claim 31, wherein the Carbohydrate is glucose, xylose, lyxose, mannose, maltose, cellobiose, galactose, or a glycosidic derivative thereof.

34. The method of claim 31, wherein the Carbohydrate is glucose or glucoside.

35. The method of claim 31, wherein the carbohydrate-containing ketone is reacted with 2, 2.1, 2.2, 2.5, 3.0, 3.5, 4.0, 5.0, 7.0, 10.0 equivalents of aldehyde.

36. The method of claim 31, further comprising reducing the compound of formula B in which each of the dotted lines is a bond and Y is O to form a compound of formula B in which at least one of the dotted lines is absent.

* * * * *